United States Patent
Ishikawa

(10) Patent No.: US 12,239,516 B2
(45) Date of Patent: Mar. 4, 2025

(54) ABSORBENT ARTICLE

(71) Applicant: DAIO PAPER CORPORATION, Ehime (JP)

(72) Inventor: Yoshitake Ishikawa, Ehime (JP)

(73) Assignee: Daio Paper Corporation, Ehime (JP)

(*) Notice: Subject to any disclaimer, the term of this patent is extended or adjusted under 35 U.S.C. 154(b) by 397 days.

(21) Appl. No.: 17/800,770

(22) PCT Filed: Mar. 9, 2021

(86) PCT No.: PCT/JP2021/009198
§ 371 (c)(1),
(2) Date: Aug. 18, 2022

(87) PCT Pub. No.: WO2021/193002
PCT Pub. Date: Sep. 30, 2021

(65) Prior Publication Data
US 2023/0110972 A1    Apr. 13, 2023

(30) Foreign Application Priority Data

Mar. 25, 2020 (JP) ................................ 2020-054787

(51) Int. Cl.
*A61F 13/15* (2006.01)
*A61F 13/535* (2006.01)
*A61F 13/53* (2006.01)

(52) U.S. Cl.
CPC .. *A61F 13/535* (2013.01); *A61F 2013/15406* (2013.01); *A61F 2013/15943* (2013.01);
(Continued)

(58) Field of Classification Search
CPC .................. A61F 13/535; A61F 13/536; A61F 2013/15406; A61F 2013/15943;
(Continued)

(56) References Cited

U.S. PATENT DOCUMENTS

2011/0313384 A1* 12/2011 Akiyama ............ A61F 13/5323
604/378
2014/0163511 A1* 6/2014 Roe ........................ A61F 13/532
604/385.101
(Continued)

FOREIGN PATENT DOCUMENTS

JP    2001-046435    2/2001
JP    2013-192848    9/2013
(Continued)

OTHER PUBLICATIONS

International Search Report for PCT/JP2021/009198, dated May 5, 2021.

*Primary Examiner* — Jacqueline F Stephens
(74) *Attorney, Agent, or Firm* — Andrus Intellectual Property Law, LLP

(57) ABSTRACT

An absorbent article wherein an upper auxiliary layer of an absorber includes a super absorbent nonwoven fabric having a surface exposed on an uppermost surface of the absorber and having a Klemm water absorptiveness of 100 mm or more, and first super absorbent polymer particles adjacent to a back surface of the super absorbent nonwoven fabric; a main absorption layer of the absorber is a cell absorbing sheet having second super absorbent polymer particles contained in cells arranged at intervals; the first super absorbent polymer particles are fixed to an upper surface of an upper sheet of the main absorption layer with an adhesive; the upper sheet is formed of a short fiber nonwoven fabric and has a larger amount of fuzz on the upper surface thereof than a lower surface thereof; and the adhesive is applied in an intermittent pattern at an application rate of 4 to 10 g/m².

7 Claims, 18 Drawing Sheets

(52) U.S. Cl.
CPC ............ *A61F 2013/530562* (2013.01); *A61F 2013/530569* (2013.01)

(58) Field of Classification Search
CPC ........ A61F 2013/530562; A61F 2013/530569; A61F 2013/5355; A61F 2013/530437; A61F 2013/53726; A61F 2013/53734; A61F 2013/53739; A61F 2013/53778
See application file for complete search history.

(56) References Cited

U.S. PATENT DOCUMENTS

2015/0250662 A1* 9/2015 Isele ................ A61F 13/51104
604/378
2018/0042782 A1* 2/2018 Konawa ................ A61F 13/534

FOREIGN PATENT DOCUMENTS

| JP | 2015226582 A | 12/2015 |
|----|--------------|---------|
| JP | 2016-199831  | 12/2016 |
| JP | 2018-015113  | 2/2018  |
| JP | 2019-017466  | 2/2019  |

* cited by examiner

[FIG.1]
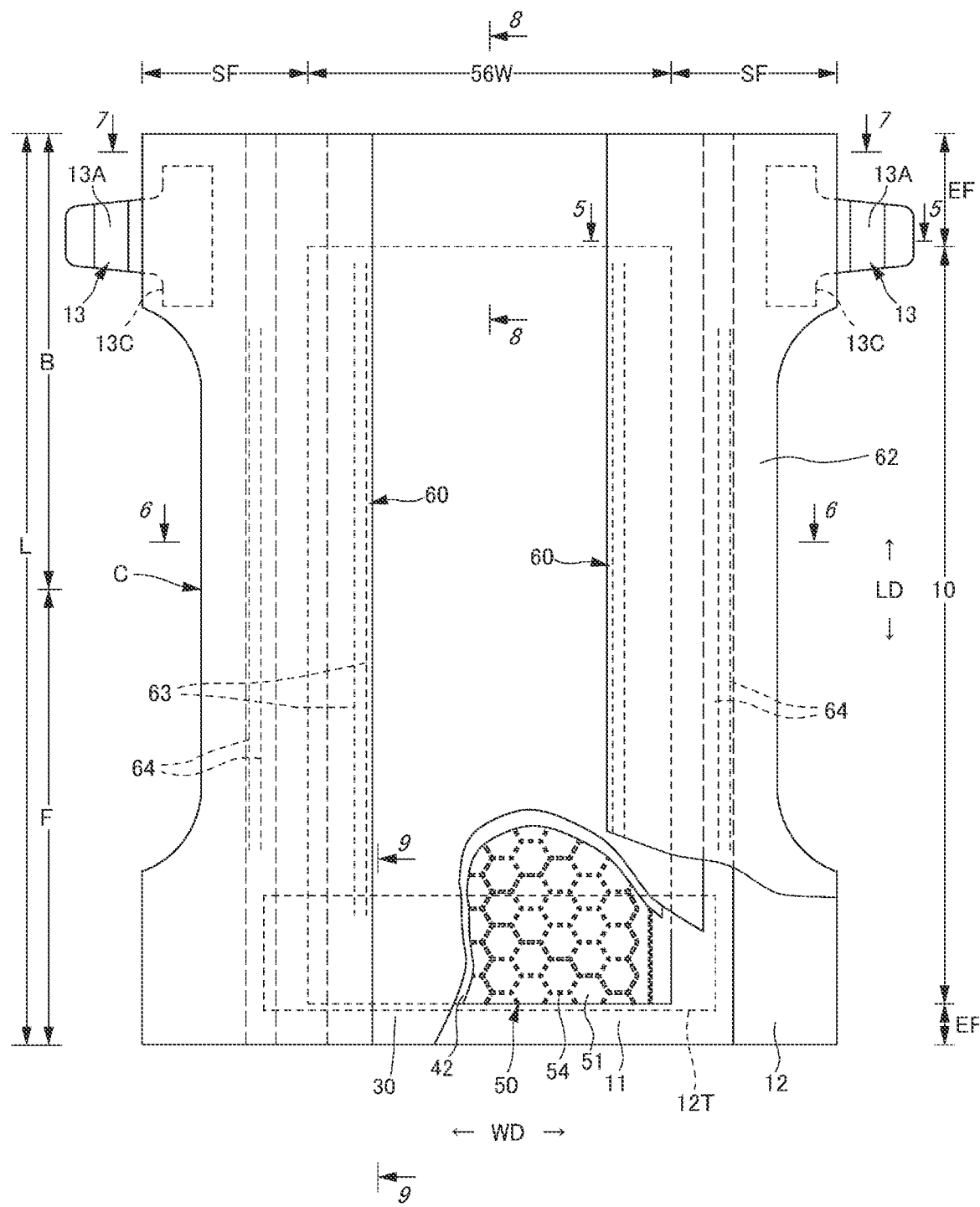

[FIG.2]
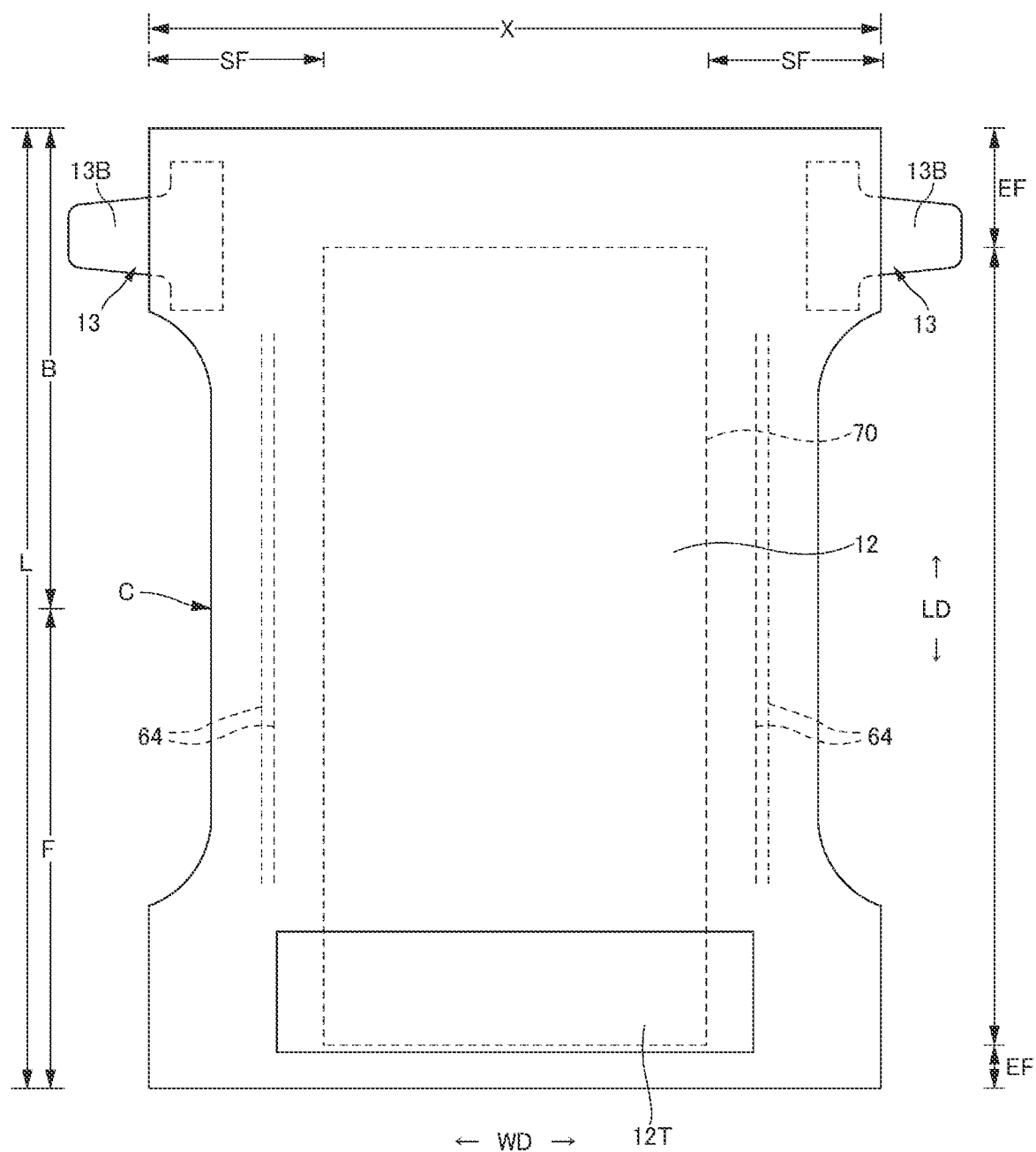

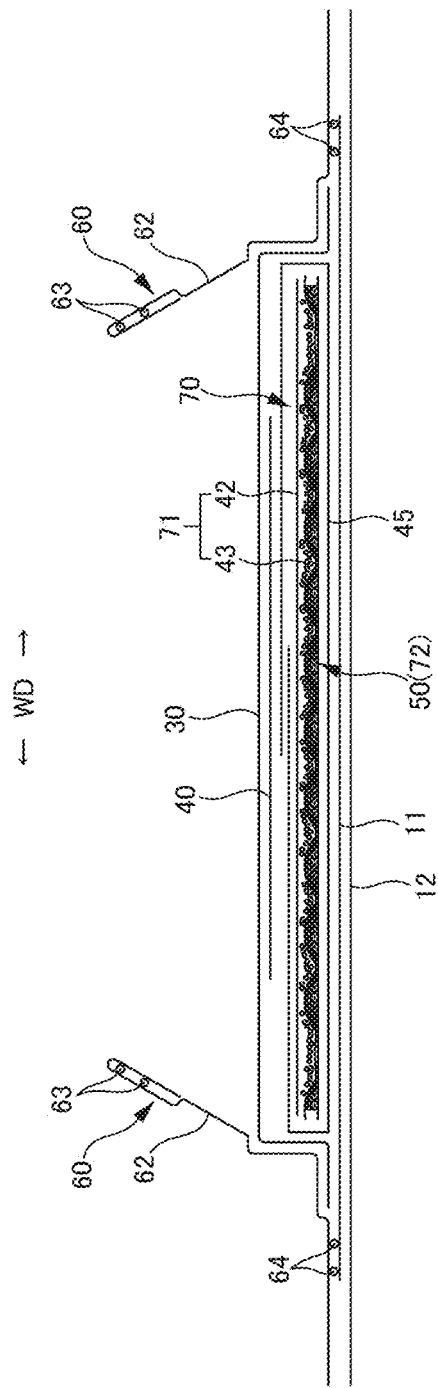

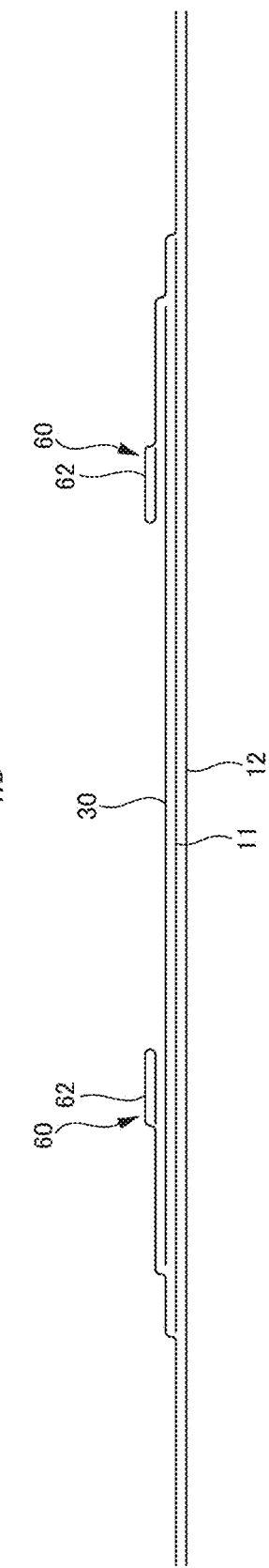

[FIG.5]
(a)
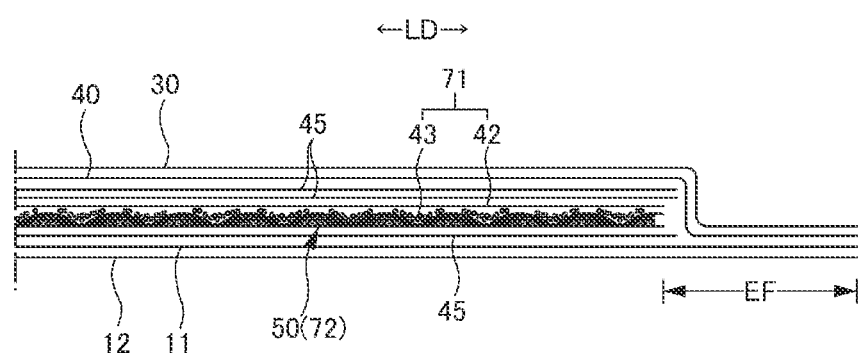
(b)
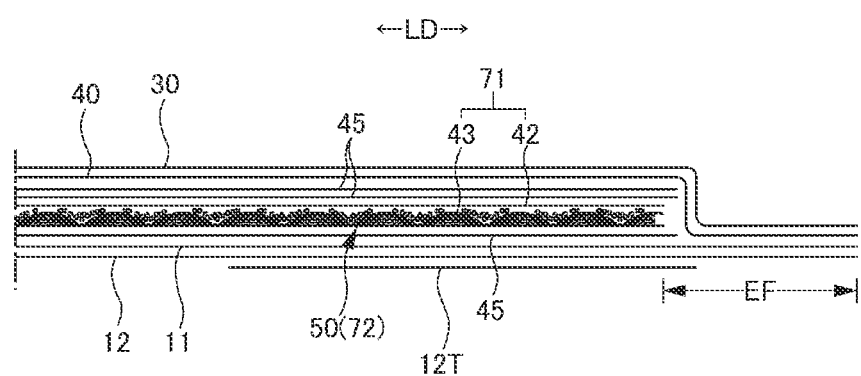

[FIG.6]
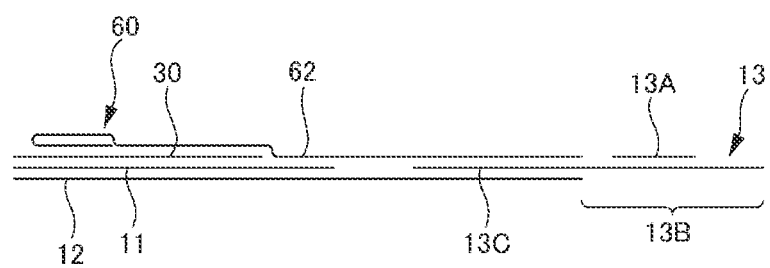

[FIG.7]
(a)
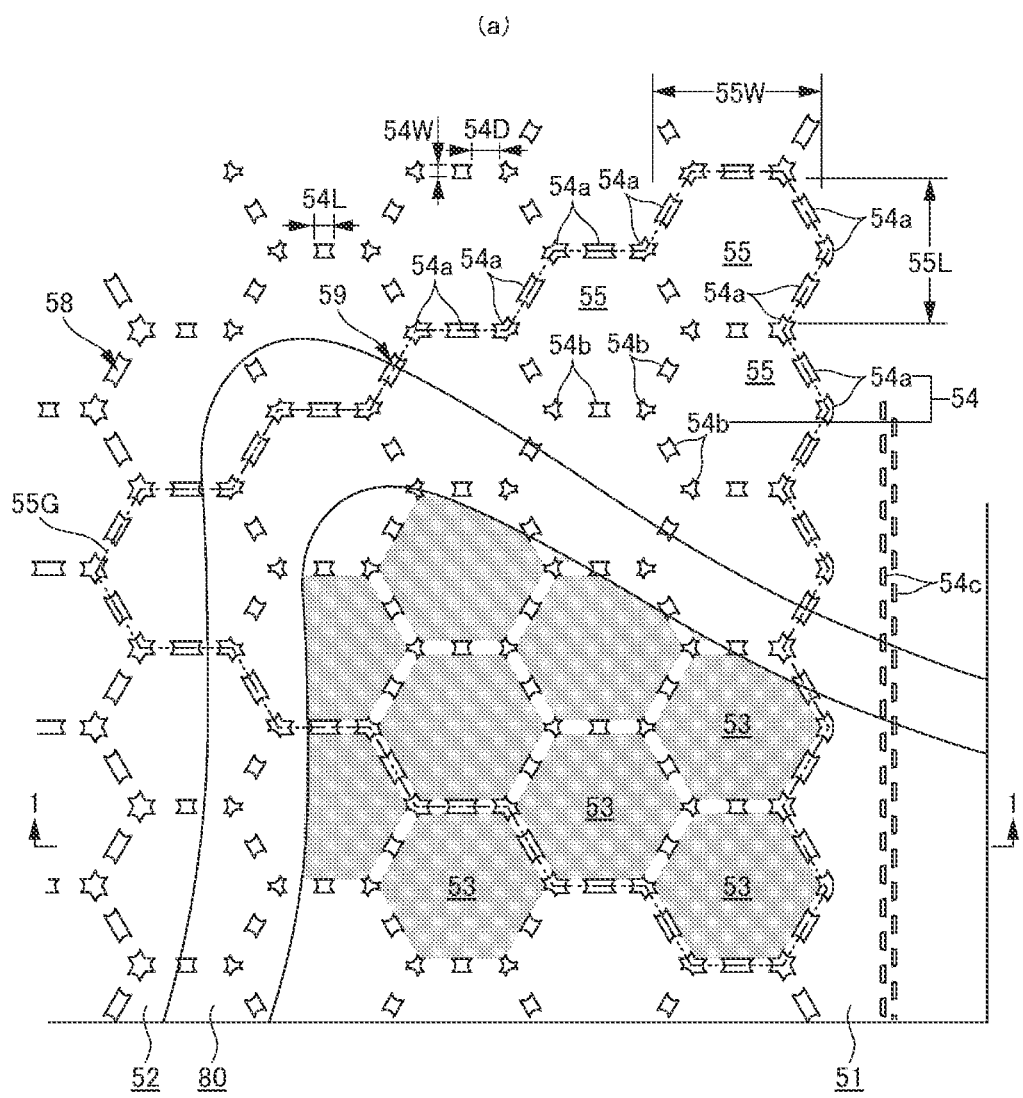
(b)
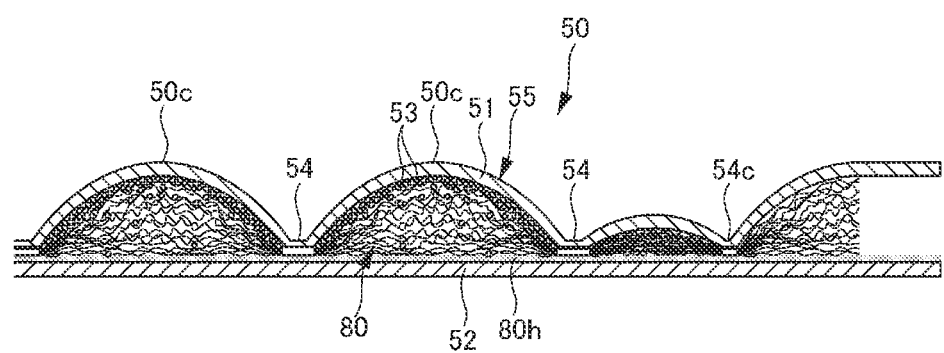

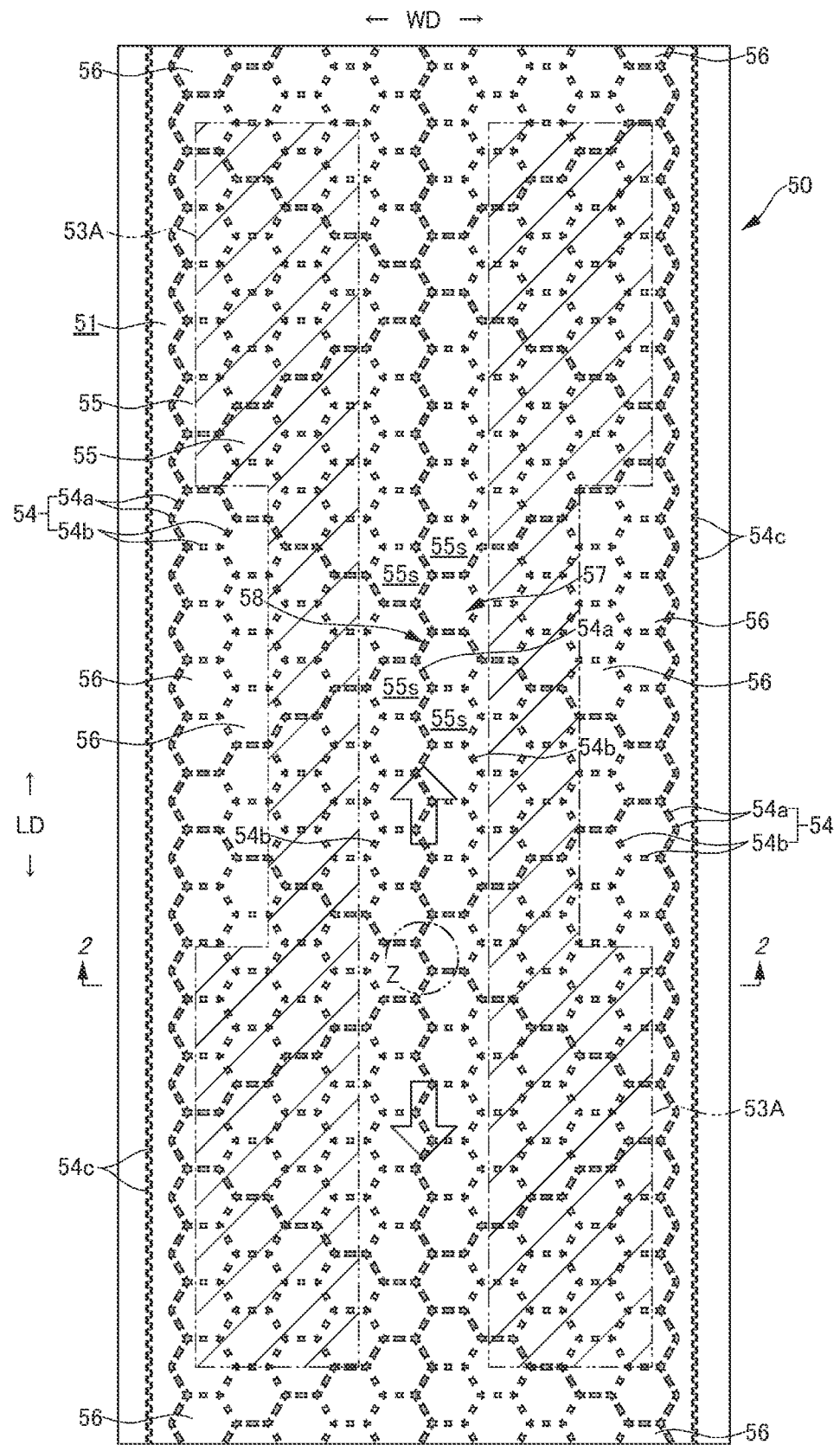
[FIG.8]

[FIG.9]
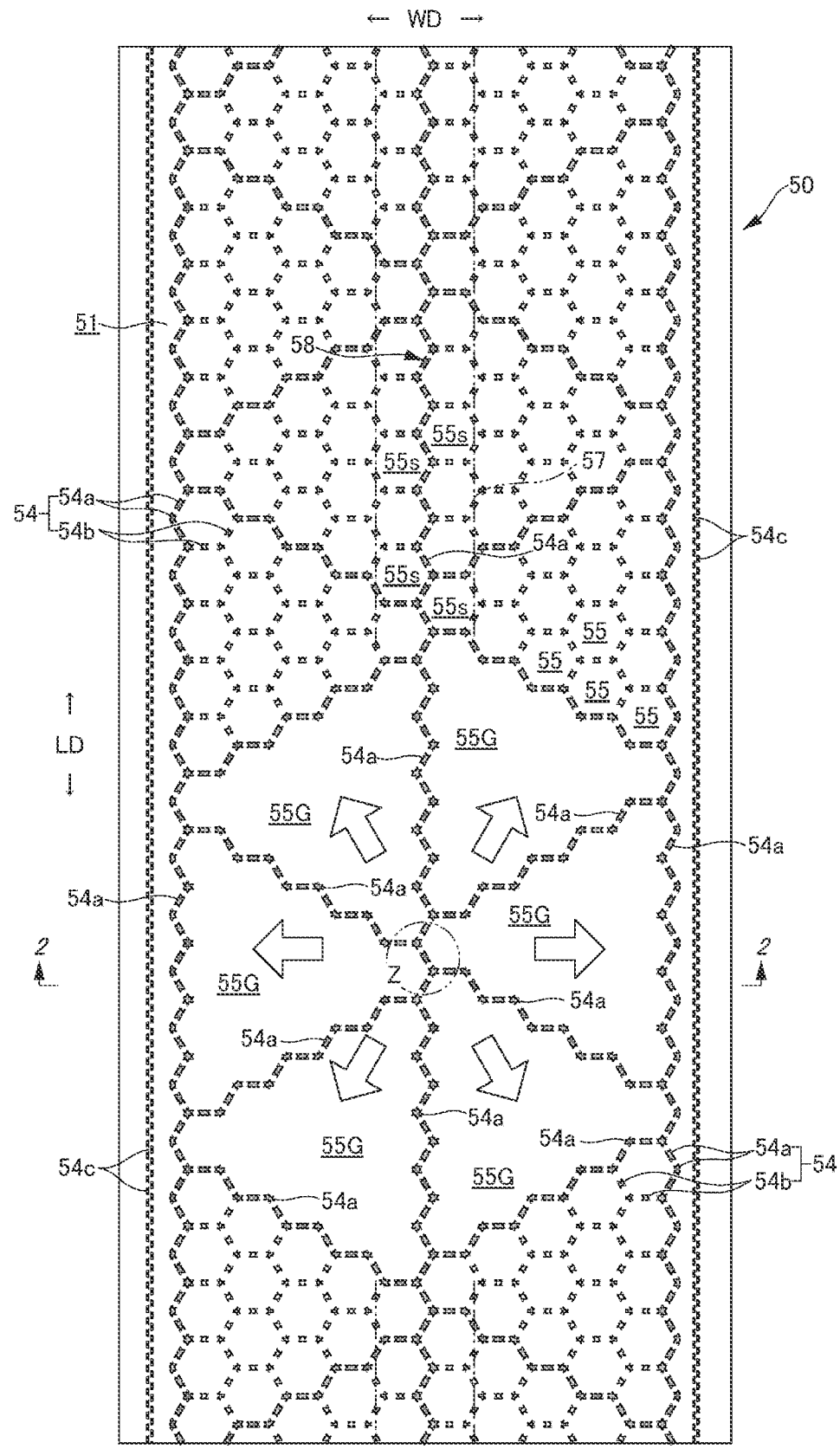

[FIG.10]
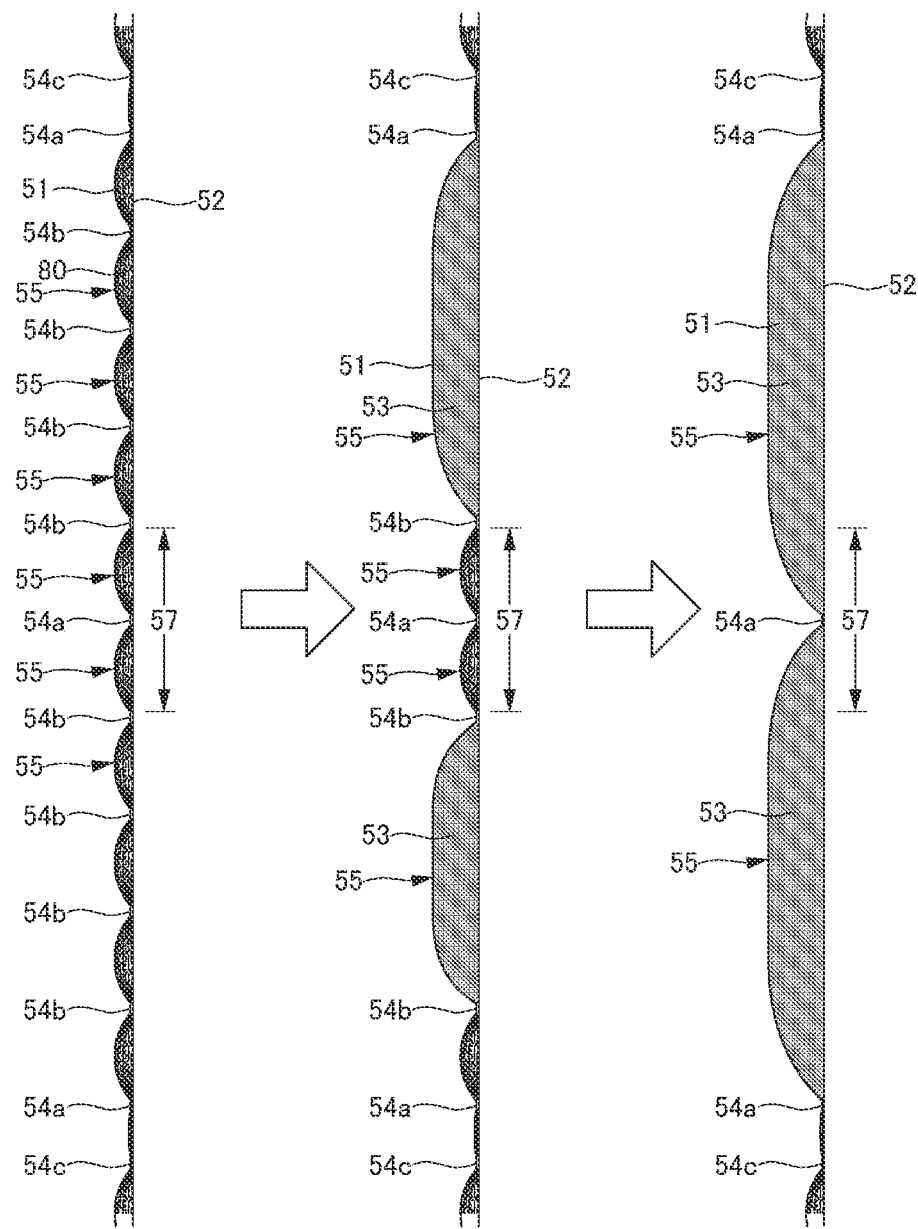

[FIG.11]
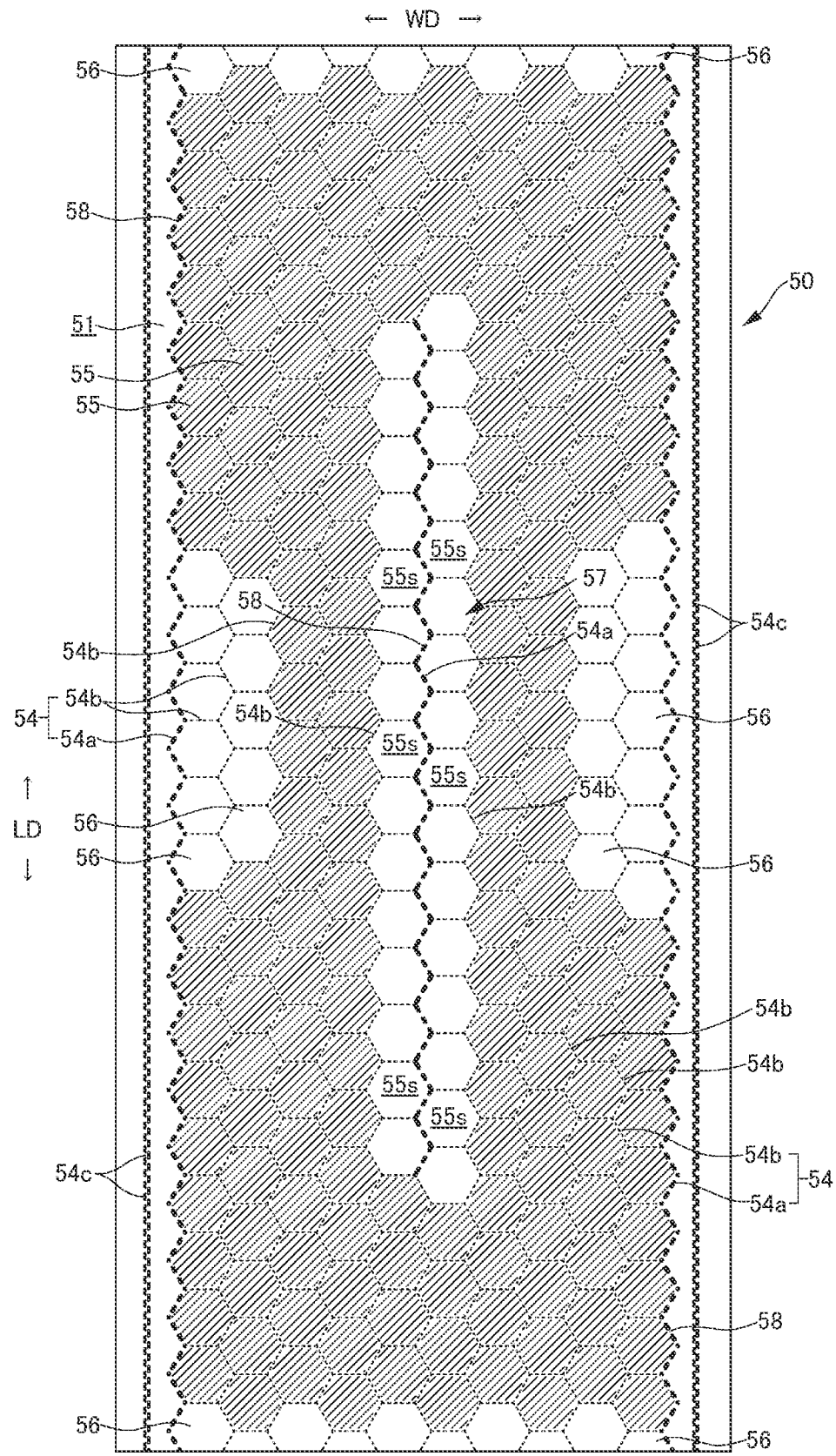

[FIG.12]
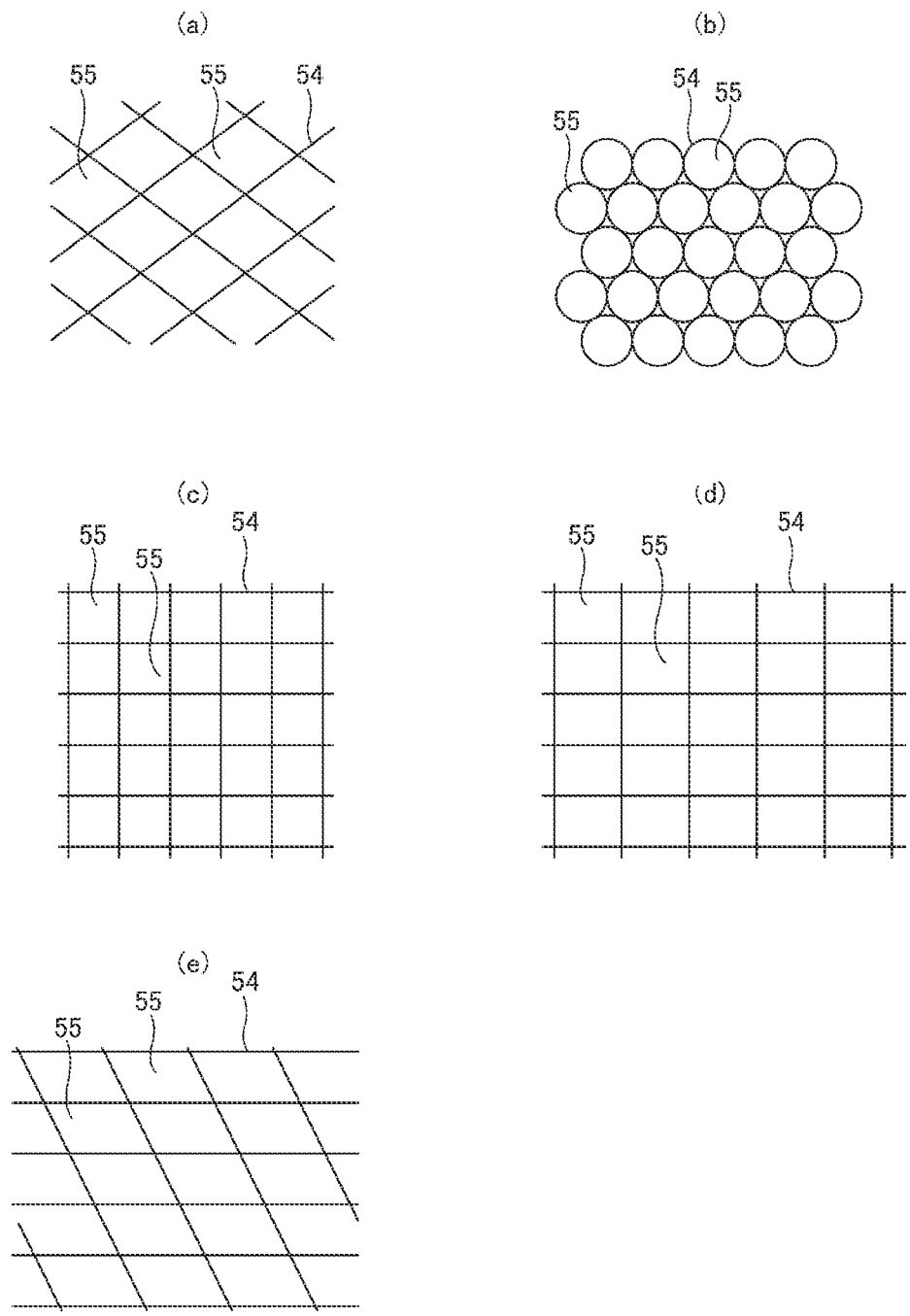

[FIG.13]
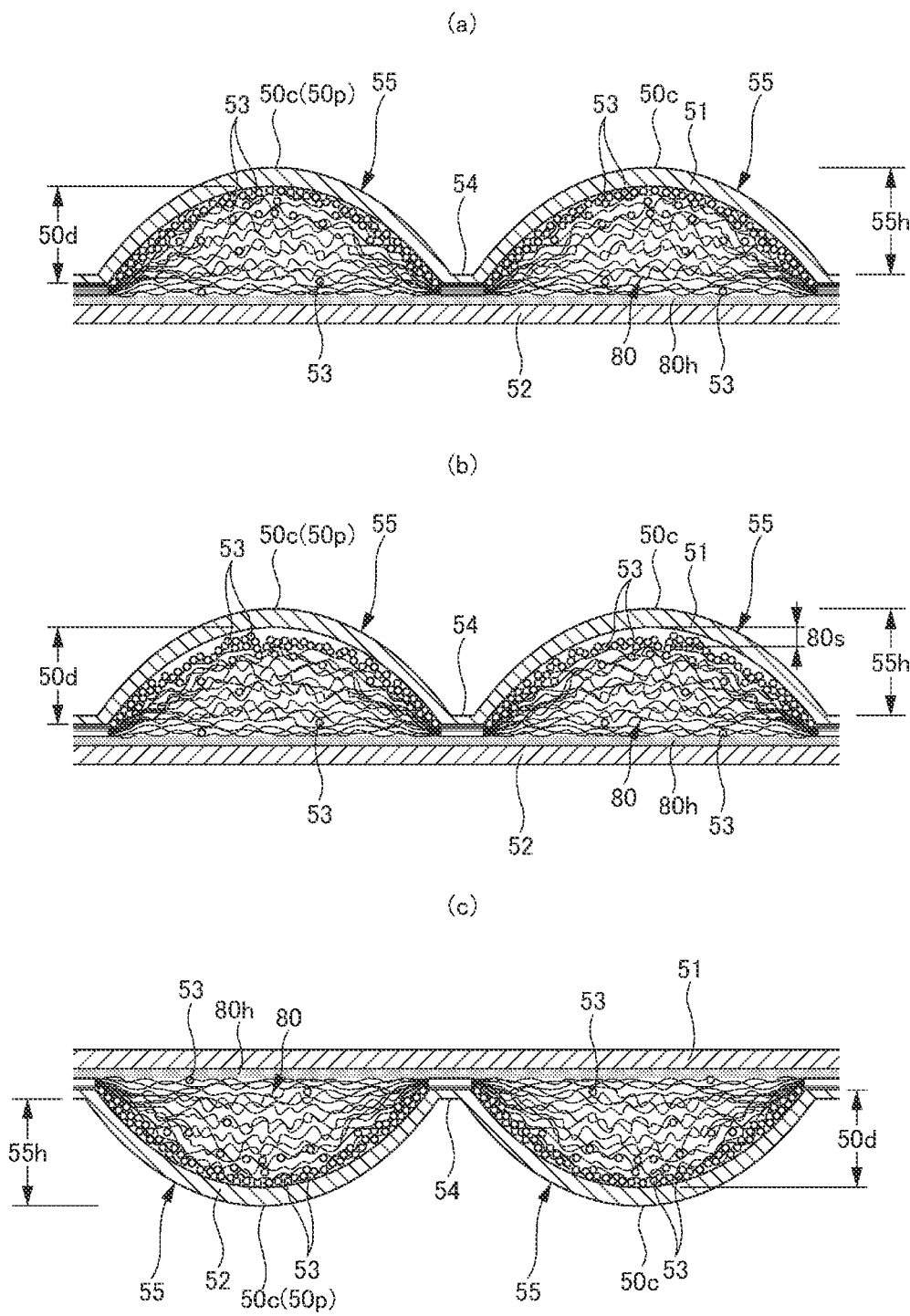

[FIG.14]
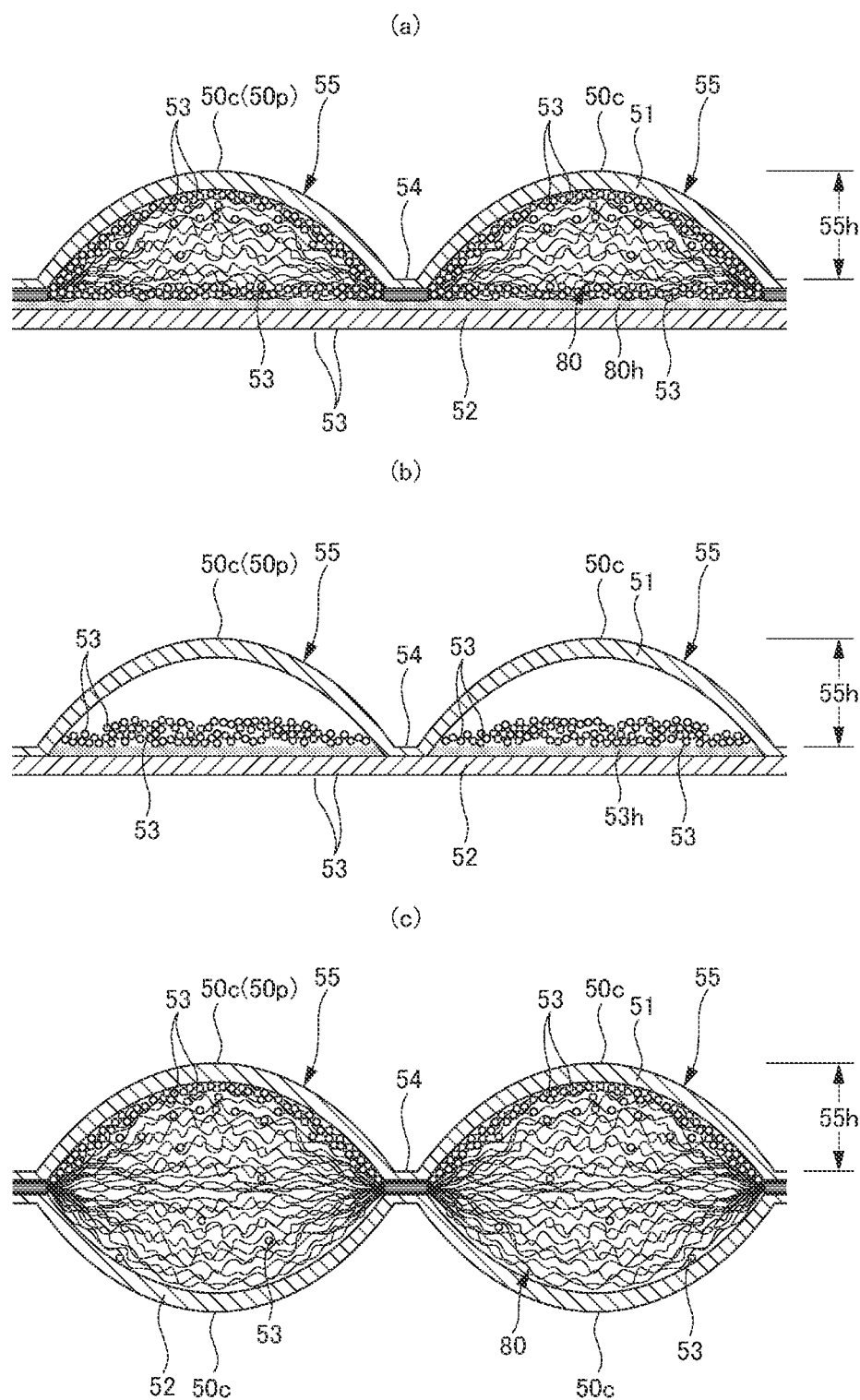

[FIG.15]
(a)
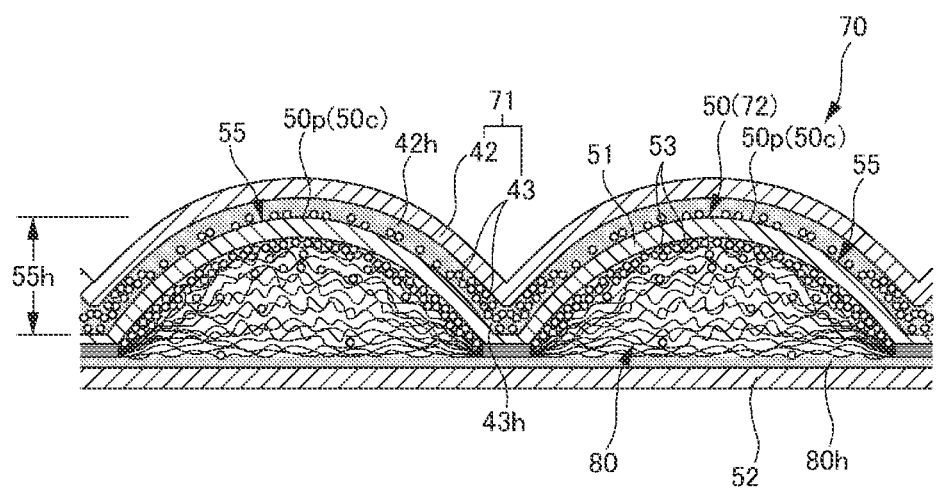
(b)
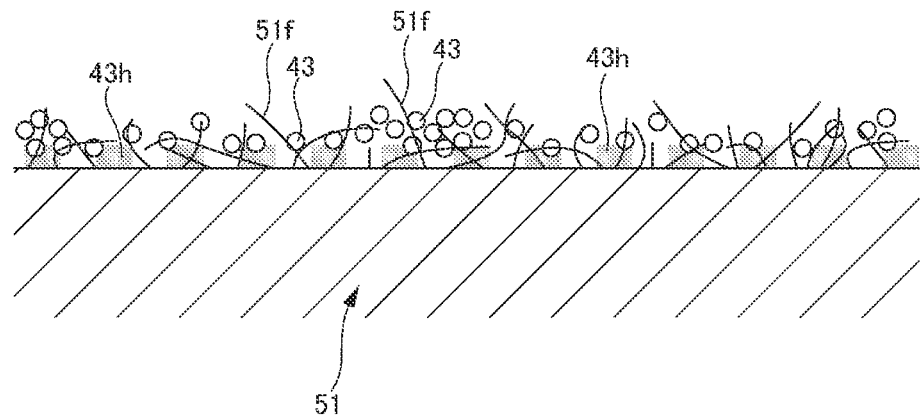

[FIG.16]
(a)
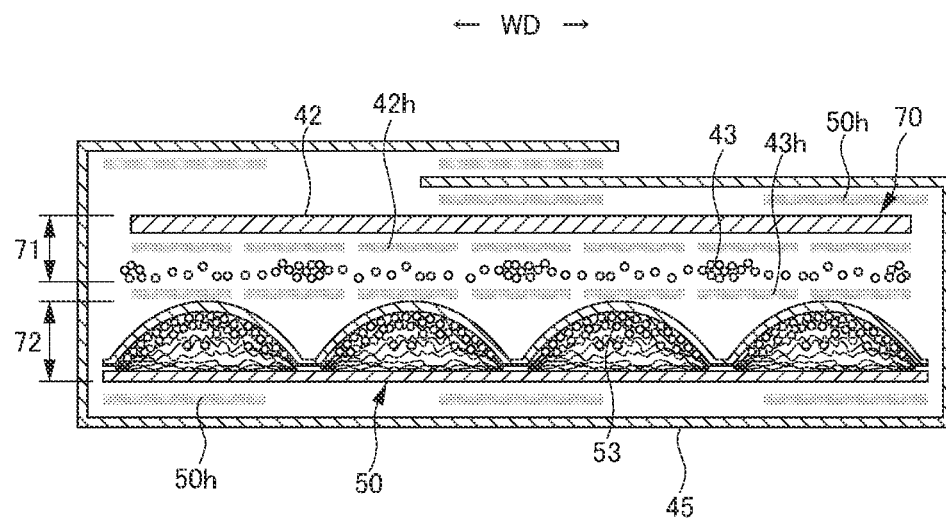
(b)
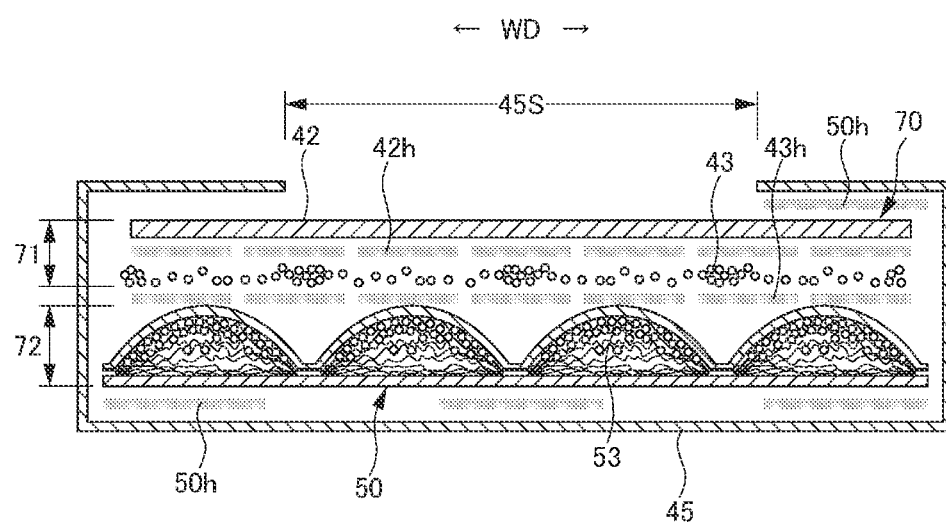

[FIG.17]
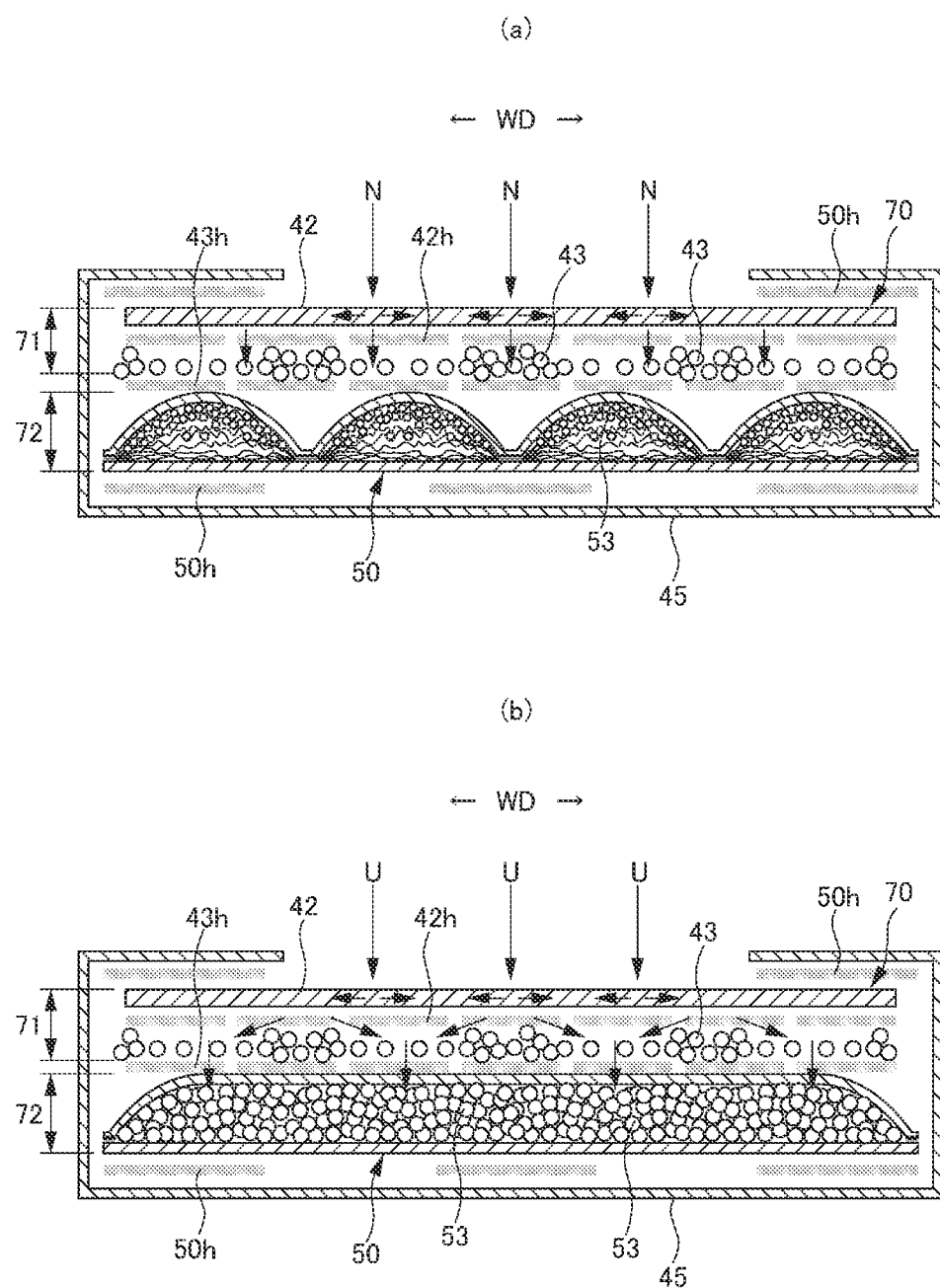

[FIG.18]
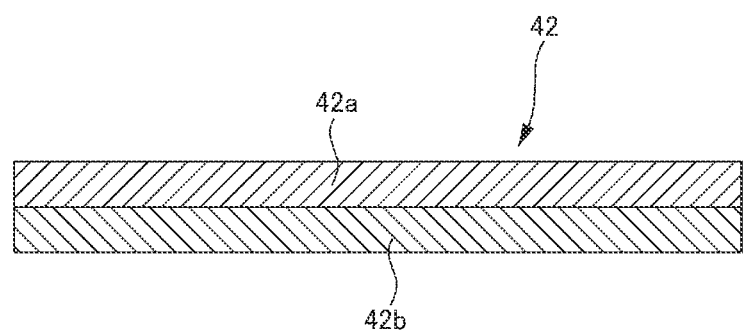

ABSORBENT ARTICLE

CROSS-REFERENCE TO RELATED APPLICATIONS

This application is the U.S. national stage application of International Application PCT/JP2021/009198, filed Mar. 9, 2021, which international application was published on Sep. 30, 2021, as International Publication WO 2021/193002 in the Japanese language. The International Application claims priority of Japanese Patent Application No. 2020-054787, filed Mar. 25, 2020. The international application and Japanese application are both incorporated herein by reference, in entirety.

TECHNICAL FIELD

The present invention relates to an absorbent article that has improved absorbability of a liquid having viscosity (hereinafter, also referred to as a viscous liquid), for example, a viscous liquid content in muddy feces or watery feces.

BACKGROUND ART

An absorbent article includes an absorber and a liquid pervious top sheet covering a front surface side of the absorber, and an excretion liquid such as urine or menstrual blood passes through the top sheet and is absorbed and retained by the absorber. As the absorber, those obtained by mixing super absorbent polymer particles (SAP) with hydrophilic short fibers such as fluff pulp and accumulating the mixture in a cotton shape are widely adopted. However, in order to meet requirements of further thinning, weight reduction, low cost, and the like while securing a sufficient absorbable amount, various absorption sheets (hereinafter, also referred to as cell absorbing sheets) each including a large number of cells (small chambers) which are surrounded by bonded portions of a liquid pervious upper sheet and a lower sheet and in which the upper sheet and the lower sheet are not bonded to each other, and a particulate material which contains super absorbent polymer particles and which is contained in the cells have been proposed (see, for example, Patent Literatures 1 to 2 below).

However, in a conventional general absorbent article, when an object to be absorbed is a viscous liquid such as a liquid content in muddy feces, watery feces, or loose feces, an absorption speed is low, the viscous liquid remains on a surface of a diaper for a certain length of time. Therefore, the viscous liquid flows and moves on the surface of the absorbent article and easily leaks from a periphery of the absorbent article disadvantageously.

Particularly, since the above mentioned cell absorbing sheet has absorption performance depending on the super absorbent polymer particles, it is suitable for absorption of a large amount of non-viscous liquid such as urine. On the other hand, since the cell absorbing sheet has a low absorption speed, it is unsuitable for absorption of a viscous liquid.

CITATION LIST

Patent Literature

Patent Literature 1: JP 2018-15113 A
Patent Literature 2: JP 2016-199831 A

SUMMARY OF INVENTION

Technical Problem

Therefore, a main object of the present invention is to achieve both of absorbability of a viscous liquid and absorption performance of a non-viscous liquid.

Solution to Problem

An absorbent article that has solved the above problem is as follows.

First Aspect

An absorbent article including: an absorber; and a liquid pervious top sheet disposed on a front surface side of the absorber, wherein
  the absorber includes an upper auxiliary layer disposed at an uppermost portion and a main absorption layer disposed on a back surface side of the upper auxiliary layer,
  the upper auxiliary layer includes a super absorbent nonwoven fabric having a surface exposed on an uppermost surface of the absorber and having a Klemm water absorptiveness of 100 mm or more, and first super absorbent polymer particles adjacent to a back surface of the super absorbent nonwoven fabric,
  the main absorption layer is a cell absorbing sheet including a liquid pervious upper sheet and a lower sheet, cells which are portions surrounded by bonded portions of the upper sheet and the lower sheet and in which the upper sheet and the lower sheet are not bonded to each other, and a particulate material which contains second super absorbent polymer particles and which is contained in the cells,
  the cells are arranged at intervals in the cell absorbing sheet,
  the first super absorbent polymer particles are fixed to an upper surface of the upper sheet of the main absorption layer with an adhesive,
  the upper sheet is formed of a short fiber nonwoven fabric and has a larger amount of fuzz on the upper surface thereof than a lower surface thereof, and
  the adhesive is applied to the upper surface in an intermittent pattern at an application rate of 4 to 10 g/m$^2$.

Action and Effect

It is a conventional general approach to improve perviousness of a viscous liquid in a layer covering a front surface side of an absorber, and it is important. However, quick permeation of the viscous liquid is promoted by quick suction by the absorber. That is, an initial absorption speed at an uppermost portion of the absorber is extremely important for absorption of the viscous liquid. The present absorbent article is based on such findings. The present absorbent article is characterized in that the upper auxiliary layer specialized for absorption of a viscous liquid is disposed on the uppermost surface of the absorber. That is, since the upper auxiliary layer includes the super absorbent nonwoven fabric having the surface exposed on the uppermost surface of the absorber and having the Klemm water absorptiveness of 100 mm or more and the first super absorbent polymer particles adjacent to the back surface of the super absorbent nonwoven fabric, while the super absorbent nonwoven fabric can quickly absorb and diffuse even the viscous liquid, the absorbed and diffused viscous liquid is delivered to the first super absorbent polymer particles adjacent to the back surface of the super absorbent nonwoven fabric so as to be absorbed and retained by the first super absorbent polymer particles. Therefore, absorbability of the viscous liquid can be remarkably improved.

In addition, if the first super absorbent polymer particles move while a product of an absorbent article is transported or used, when a user touches an external surface of the absorbent article with a hand, gritty and uncomfortable feeling of the first super absorbent polymer particles is likely to be transmitted to the hand. In order to prevent occurrence of such a problem, it is preferable that most of the first super absorbent polymer particles of the upper auxiliary layer is fixed on the upper surface of the upper sheet via the adhesive. However, in this case, the absorber becomes hard as an application amount of the adhesive is increased. Not only that, but when the first super absorbent polymer particles absorb the liquid to be expanded, the increased application amount of the adhesive inhibits such expansion of the first super absorbent polymer particles such that the first super absorbent polymer particles may be unlikely to attain the original absorption performance. Further, when a non-viscous liquid such as urine is absorbed, it is likely to be difficult for the non-viscous liquid to be supplied from the upper auxiliary layer to the main absorption layer, because the adhesive inhibits the permeation of the non-viscous liquid. As a result, the adhesive may be likely to inhibit the absorption by the main absorption layer.

On the other hand, in the present absorbent article, as for the adhesive for fixing the first super absorbent polymer particles to the upper surface of the upper sheet, by suppressing the application amount of the adhesive and by applying the adhesive in the intermittent pattern, the permeation of the non-viscous liquid to the main absorption layer can be unlikely to be inhibited. Nevertheless, only by the above measures, a situation is caused in which the first super absorbent polymer particles easily move. However in the present absorbent article, since the upper sheet is formed of the short fiber nonwoven fabric and has a larger amount of fuzz on the upper surface thereof than the lower surface thereof, the first super absorbent polymer particles are captured among the fuzz (projected fibers) such that the movement of the first super absorbent polymer particles is suppressed, and additionally, the fuzz existing among the first super absorbent polymer particles makes it possible that the absorption of the viscous liquid and the permeability of the non-viscous liquid are unlikely to be inhibited.

Second Aspect

The absorbent article according to the first aspect, wherein in the first super absorbent polymer particles, a ratio of particles having a particle size of more than 500 μm is 30% by weight or less, the ratio of particles having a particle size of 500 μm or less and more than 180 μm is 60% by weight or more, the ratio of particles having a particle size of more than 106 μm and 180 μm or less is 10% by weight or less, and the ratio of particles having a particle size of 106 μm or less is 10% by weight or less, and a basis weight of the first super absorbent polymer particles on the upper surface of the upper sheet is 40 to 100 g/m².

Action and Effect

The particle sizes and basis weight of the first super absorbent polymer particles can be appropriately determined, but when the adhesion amount of the first super absorbent polymer particles is too large, many first super absorbent polymer particles cannot be fixed via the adhesive, these unfixed first super absorbent polymer particles easily move. Not only that, but the first super absorbent polymer particles preferentially absorb the liquid to be expanded, and gel blocking easily occurs in which the expanded first super absorbent polymer particles adhere each other to form a hardly liquid pervious layer. On the other hand, if the particle sizes and the basis weight of the first super absorbent polymer particles fall within the ranges defined in the present aspect, even the above mentioned application amount of the adhesive is applied in the intermittent pattern, the first super absorbent polymer particles can be sufficiently fixed. In addition, even after the first super absorbent polymer particles of the upper auxiliary layer sufficiently absorb the liquid to be expanded, a portion where gel blocking does not occur remains, and supply of the non-viscous liquid to the main absorption layer can be secured, which is preferable.

Third Aspect

The absorbent article according to the second aspect, wherein a basis weight of the second super absorbent polymer particles in the main absorption layer is 150 to 350 g/m².

Action and Effect

In the present absorbent article, since the first super absorbent polymer particles are contained in the upper auxiliary layer, the basis weight of the second super absorbent polymer particles can be suppressed at a low level in the main absorption layer as in the present aspect. Thus, when a user touches an external surface of the absorbent article with a hand, a gritty touch (uncomfortable feeling) of the second super absorbent polymer particles is unlikely to be transmitted to the hand.

Fourth Aspect

The absorbent article according to any one of the first to third aspects, wherein
the upper sheet is formed of an air through nonwoven fabric having a basis weight of 17 to 40 g/m² and a thickness of 0.2 to 0.7 mm, and
an air-sprayed surface of the air through nonwoven fabric corresponds to the upper surface of the upper sheet.

Action and Effect

As the short fiber nonwoven fabric having a larger amount of fuzz on the upper surface thereof than the lower surface thereof, a nonwoven fabric may be appropriately used whose fuzz is formed by a raising process. However, since this process requires a high cost, it is preferable to use the air through nonwoven fabric as in the present aspect. As is known in the art, an air through nonwoven fabric is formed by a process in which short fibers are accumulated onto a net to form a web and after that, these short fibers are weld-bonding to each other by heated air (hot air) forced through the web. In the air through nonwoven fabric, the air-sprayed surface (the surface to which heated air is sprayed) is fluffier than a net surface. Therefore, by using the air-sprayed surface of the air-through nonwoven fabric as the upper surface of the upper sheet, the movement of the first super absorbent polymer particles can be suppressed by the fuzz provided originally on the upper surface of the upper sheet without the raising process.

Fifth Aspect

The absorbent article according to the fourth aspect, wherein the air-sprayed surface of the air through nonwoven fabric includes hollow fibers having a fineness of 2.0 to 7.0 dtex.

Action and Effect

The air through nonwoven fabric including sufficiently fine hollow fibers in the air-sprayed surface is preferable due to a particularly fluffy air-sprayed surface.

Advantageous Effects of Invention

According to the present invention, for example, it is possible to achieve both of absorbability of a viscous liquid and absorption performance of a non-viscous liquid.

BRIEF DESCRIPTION OF DRAWINGS

FIG. 1 is a plan view illustrating an internal surface of a tape-type disposable diaper in a state where the diaper is spread.

FIG. 2 is a plan view illustrating an external surface of a tape-type disposable diaper in a state where the diaper is spread.

FIG. 3 is a cross-sectional view cut along 6-6 of FIG. 1.

FIG. 4 is a cross-sectional view cut along 7-7 of FIG. 1.

FIG. 5(a) is a cross-sectional view cut along 8-8 of FIG. 1, and FIG. 5(b) is a cross-sectional view cut along 9-9 of FIG. 1.

FIG. 6 is a cross-sectional view cut along 5-5 of FIG. 1.

FIG. 7(a) is a broken bottom view of a main part of an absorber, and FIG. 7(b) is a cross-sectional view cut along 1-1 of FIG. 7(a).

FIG. 8 is a plan view of an absorber.

FIG. 9 is a plan view of an absorber.

FIG. 10 is a cross-sectional view cut along 2-2 of FIGS. 8 and 9.

FIG. 11 is a plan view of an absorber illustrating a bonded portion in a simplified manner.

FIG. 12 is a schematic plan view illustrating various arrangement examples of cells.

FIG. 13 is a cross-sectional view of various cell absorbing sheets.

FIG. 14 is a cross-sectional view of various cell absorbing sheets.

FIG. 15(a) is a cross-sectional view illustrating a main part of an absorber and FIG. 15(b) is a cross-sectional view illustrating schematically super absorbent polymer particles fixed on the upper sheet.

FIG. 16 is a cross-sectional view illustrating a layered structure of an absorber and a wrapping sheet.

FIG. 17 is a cross-sectional view illustrating a change at the time of absorption.

FIG. 18 is a cross-sectional view schematically illustrating a layered structure of a super absorbent nonwoven fabric.

DESCRIPTION OF EMBODIMENTS

Hereinafter, as an example of the absorbent article, a tape-type disposable diaper will be described with reference to the attached drawings. FIGS. 1 to 6 illustrate an example of a tape-type disposable diaper, in which a reference character X indicates the maximum width of the diaper excluding fastening tapes, and a reference character L indicates the maximum length of the diaper. Note that components adjacent in a thickness direction are fixed or bonded to each other as necessary in a similar manner to a known diaper also at a portion other than a fixed or bonded portion described below. A dotted pattern portion in each of the cross-sectional views indicates an adhesive such as a hot melt adhesive as the fixing or bonding means. The hot melt adhesive can be applied by a known method such as slot application, bead application into a continuous line or dot shape, spray application into a spiral shape, a Z shape, or a wave shape, or pattern coating (transfer of a hot melt adhesive by a letterpress method). Alternatively or in addition, in a fixed portion of an elastic member, the hot melt adhesive can be applied to an outer peripheral surface of the elastic member, and the elastic member can be fixed to an adjacent member. Examples of the hot melt adhesive include an EVA-based agent, a pressure sensitive adhesive rubber-based agent (elastomer-based agent), a polyolefin-based agent, and a polyester/polyamide-based agent, and these can be used without particular limitation. As a fixing or bonding means for bonding components to each other, a means by material welding such as heat sealing or ultrasonic sealing can also be used. In a portion where a pervious property in a thickness direction is required, components adjacent in the thickness direction are fixed or bonded to each other in an intermittent pattern. For example, when such intermittent fixing or bonding is performed with a hot melt adhesive, intermittent pattern application in a spiral shape, a Z shape, a wave shape, or the like can be suitably used, and when application is performed in a range larger than an application width by one nozzle, a plurality of intermittent pattern applications in a spiral shape, a Z shape, a wave shape, or the like can be performed with or without a space in a width direction.

The tape-type disposable diaper has a basic structure in which an absorber 70 is interposed between a liquid pervious top sheet and a liquid impervious sheet located on a back surface side. In addition, the tape-type disposable diaper includes a pair of end flaps EF which are portions each extending to each of a front side and a back side of the absorber 70 and not including the absorber 70, and a pair of side flaps SF extending laterally from side edges of the absorber 70. Both side edges of the side flaps SF each have a narrowing portion along a periphery of a leg, but may be linear. Each of the side flaps SF of a dorsal side portion B has a fastening tape 13, and when the diaper is worn, the fastening tape 13 is engaged at an appropriate position on an external surface of a ventral side portion F in a state where the side flap SF of the dorsal side portion B is superimposed on an outer side of the side flap SF of the ventral side portion F.

In addition, in the tape-type disposable diaper, the entire external surface other than the fastening tapes 13 is formed of an exterior nonwoven fabric 12. In particular, in a region including the absorber 70, a liquid impervious sheet 11 is fixed to an internal surface side of the exterior nonwoven fabric 12 with an adhesive such as a hot melt adhesive. Furthermore, on an internal surface side of the liquid impervious sheet 11, the absorber 70, an intermediate sheet 40, and a top sheet 30 are stacked in this order. The top sheet 30 and the liquid impervious sheet 11 are rectangular in the illustrated example, and each have a size slightly larger than the absorber 70 in a front-back direction LD and a width direction WD. A peripheral edge portion protruding from a side edge of the absorber 70 in the top sheet 30 is bonded to a peripheral edge portion protruding from a side edge of the absorber 70 in the liquid impervious sheet 11 with a hot melt adhesive or the like. In addition, the liquid impervious sheet 11 is formed so as to be slightly wider than the top sheet 30.

Furthermore, on each side of the tape-type disposable diaper, a rising gather 60 rising up to a skin side of a wearer is formed, and a gather sheet 62 forming the rising gather 60 is fixed in a range extending from a top of each side portion of the top sheet 30 to an internal surface of each side flap SF.

Hereinafter, details of each component will be described in order. Note that as a nonwoven fabric in the following description, a known nonwoven fabric can be appropriately used according to a site or a purpose. Examples of a constituent fiber of the nonwoven fabric include, but are not limited to, a synthetic fiber such as a polyolefin-based fiber including polyethylene and polypropylene, a polyester-based fiber, or a polyamide-based fiber (including a composite fiber such as core-sheath in addition to a single component fiber), a regenerated fiber such as rayon or cupra, and a natural fiber such as cotton. These fibers can be mixed and used. In order to enhance flexibility of the nonwoven fabric, it is preferable to use a crimped fiber as the constituent fiber. In addition, the constituent fiber of the nonwoven fabric may be a hydrophilic fiber (including a fiber that has become hydrophilic by a hydrophilizing agent), a hydrophobic fiber, or a water-repellent fiber (including a fiber that has become water-repellent by a water repellent agent). In addition, the nonwoven fabric is generally classified into a short fiber nonwoven fabric, a long fiber nonwoven fabric, a spunbonded nonwoven fabric, a meltblown nonwoven fabric, a spunlace nonwoven fabric, a thermal bond (air through) nonwoven fabric, a needle punch nonwoven fabric, a point bond nonwoven fabric, a laminated nonwoven fabric (an SMS nonwoven fabric, an SMMS nonwoven fabric, or the like having a meltblown layer sandwiched between spunbond layers), and the like depending on a fiber length, a sheet forming method, a fiber bonding method, and a stacked structure, and any of these nonwoven fabrics can be used.

(Exterior Nonwoven Fabric)

The exterior nonwoven fabric 12 constitutes a product external surface, and is for making the product external surface have a cloth-like appearance and touch. It is desirable that the exterior nonwoven fabric has a fiber basis weight of 10 to 50 g/m$^2$, particularly 15 to 30 g/m$^2$. The exterior nonwoven fabric 12 can be omitted, and in this case, the liquid impervious sheet 11 can have the same shape as the exterior nonwoven fabric 12 to constitute the product external surface.

(Liquid Impervious Sheet)

A material of the liquid impervious sheet 11 is not particularly limited, but examples thereof include a polyolefin-based resin such as polyethylene or polypropylene, a laminated nonwoven fabric obtained by stacking a nonwoven fabric on a polyethylene sheet or the like, and a nonwoven fabric in which a waterproof film is interposed to substantially secure a liquid impervious property (in this case, the waterproof film and the nonwoven fabric form a liquid impervious sheet). Of course, in addition to these materials, a liquid impervious and moisture permeable material that has been favorably used from a viewpoint of preventing stuffiness in recent years can be used, for example. Examples of a sheet of the liquid impervious and moisture permeable material may include a microporous sheet obtained by kneading an inorganic filler in a polyolefin-based resin such as polyethylene or polypropylene, molding the kneaded mixture into a sheet, and stretching the sheet in one or two axial directions. Furthermore, a nonwoven fabric using a micro denier fiber, and a sheet that has become liquid impervious without using a waterproof film by a method for reinforcing leakproofness by reducing a space between fibers by applying heat and pressure, or a method for applying a super absorbent resin, a hydrophobic resin, or a water repellent agent, can be used as the liquid impervious sheet 11.

(Top Sheet)

The top sheet 30 is liquid permeable, and examples thereof include a perforated or imperforated nonwoven fabric and a porous plastic sheet. Both sides of the top sheet 30 may be folded back to a back surface side of the absorber 70 or may protrude laterally from side edges of the absorber 70 without being folded back as in the illustrated example.

For the purpose of preventing positional deviation with respect to a back surface side member or the like, it is desirable that the top sheet 30 is fixed to a member adjacent to the back surface side by a bonding means by material welding such as heat sealing or ultrasonic sealing, or with a hot melt adhesive. In the illustrated example, the top sheet 30 is fixed to a surface of an intermediate sheet 40 and a surface of a portion located on a front surface side of the absorber 70 in a wrapping sheet 45 with a hot melt adhesive applied to a back surface of the top sheet 30.

(Intermediate Sheet)

The intermediate sheet 40 is bonded to a back surface of the top sheet 30 in order to quickly move an excretion liquid that has passed through the top sheet 30 toward the absorber 70 and to prevent returning. For bonding the intermediate sheet 40 to the top sheet 30, heat embossing or ultrasonic welding can be used in addition to a hot melt adhesive.

As the intermediate sheet 40, a resin film having a large number of transmission holes can be used in addition to a nonwoven fabric. As the nonwoven fabric, a similar material to the top sheet 30 can be used, but those having higher hydrophilicity than the top sheet 30 or those having a higher fiber density than the top sheet 30 are preferable because of excellent liquid movement characteristics from the top sheet 30 to the intermediate sheet 40. For example, an air through nonwoven fabric can be suitably used as the intermediate sheet 40. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m$^2$, and more preferably 25 to 60 g/m$^2$. A raw material fiber of the nonwoven fabric preferably has a fineness of 2.0 to 10 dtex. In order to make the nonwoven fabric bulky, as all of constituent fibers or some of mixed fibers, eccentric fibers having no core in the center, hollow fibers, eccentric and hollow fibers are also preferably used.

The intermediate sheet 40 in the illustrated example is disposed at the center so as to be shorter than the width of the absorber 70, but may be disposed over the maximum width. The size of the intermediate sheet 40 in the front-back direction LD may be the same as the maximum length of the diaper, may be the same as the size of the absorber 70, or may be within a short length range centered on a liquid receiving region.

(Rising Gather)

In order to prevent lateral movement of excrement on the top sheet 30 and to prevent side leakage, it is preferable that the rising gather 60 is disposed to protrude (rise) from an internal surface of the product on each side in the width direction WD.

The rising gather 60 includes the gather sheet 62 and an elongated gather elastic member 63 fixed to the gather sheet 62 in a stretched state in the front-back direction LD. A water repellent nonwoven fabric can be used as the gather sheet 62, and a rubber thread or the like can be used as the elastic member 63. As illustrated in FIGS. 1 and 3, a plurality of elastic members may be disposed on each side, or one elastic member may be disposed on each side.

An internal surface of the gather sheet 62 has a fixed start point in the width direction WD on a side portion of the top sheet 30, and that portion of the gather sheet 62 which is located outside the fixed start point in the width direction WD is fixed, with a hot melt adhesive or the like, to a side portion of the liquid impervious sheet 11 and a side portion of the exterior nonwoven fabric 12 located at the portion outside from the fixed start point.

In a periphery of a leg, that portion of the rising gather 60 which is located inside the fixed start point in the width direction WD is fixed to the top sheet 30 at both end portions in a product front-back direction LD. However, a portion therebetween is a non-fixed free portion, and the free portion rises by a contraction force of the elastic member 63. When the diaper is worn, the diaper is attached to the body of a wearer in a boat shape, and a contraction force of the elastic member 63 acts. Therefore, the rising gather 60 rises by the contraction force of the elastic member 63 and fits closely to the periphery of the leg. As a result, so-called side leakage therefrom is prevented.

Unlike the illustrated example, both end portions in the front-back direction LD in an internal portion of the gather sheet 62 in the width direction WD can be fixed in a two-folded state having a base edge side portion extending inward from an outer portion in the width direction WD and a tip side portion folded back to a body side from an end edge of the base edge side portion on the central side in the width direction WD and extending outward in the width direction WD, and a portion therebetween can be a non-fixed free portion.

(Planar Gather)

As illustrated in FIGS. 1 to 3, in each side flap SF, on an outer side in the width direction WD in the vicinity of the fixed start point of the fixed portion of the gather sheet 62, between the gather sheet 62 and the liquid impervious sheet 11, a leg periphery elastic member 64 made of an elongated elastic member such as rubber thread is fixed in a state of being extended in the front-back direction LD, and a leg periphery portion of each side flap SF is constituted as a planar gather. The leg periphery elastic member 64 can also be disposed between the liquid impervious sheet 11 and the exterior nonwoven fabric 12 in the side flap SF. A plurality of the leg periphery elastic members 64 may be disposed on each side as in the illustrated example, or only one leg periphery elastic member 64 may be disposed on each side.

(Fastening Tape)

As illustrated in FIGS. 1, 2, and 6, the fastening tape 13 includes: a sheet base material forming a tape attachment portion 13C fixed to a side portion of the diaper and a tape main unit portion 13B protruding from the tape attachment portion 13C; and a ventral side engagement portion 13A disposed in a width direction WD intermediate portion of the tape main unit portion 13B in the sheet base material, and a tip side portion of the engagement portion 13A is a tab part. The tape attachment portion 13C of the fastening tape 13 is sandwiched between the gather sheet 62 forming an inner layer and the exterior nonwoven fabric 12 forming an outer layer in the side flap SF, and is bonded to these sheets with a hot melt adhesive. In addition, the engagement portion 13A is fixed to the sheet base material with an adhesive.

As the engagement portion 13A, a hook member (male member) of a mechanical fastener (hook and loop fastener) is suitable. The hook member has a large number of engaging projections on an external surface side thereof. Examples of the shapes of the engaging projections include a tick shape, a J shape, a mushroom shape, a T shape, and a double J shape (a shape in which J-shaped ones are connected to each other back to back), but any one of these shapes may be used. Of course, an adhesive material layer can be disposed as an engagement portion of the fastening tape 13.

In addition, as the sheet base material forming from the tape attachment portion 13C to the tape main unit portion 13B, in addition to various nonwoven fabrics such as a spunbonded nonwoven fabric, an air through nonwoven fabric, and a spunlace nonwoven fabric, a plastic film, a polylaminated nonwoven fabric, paper, or a composite material thereof can be used.

(Target Sheet)

A target sheet 12T having a target for facilitating engagement is preferably disposed at a part to be engaged with the fastening tape 13 in the ventral side portion F. In a case where the engagement portion 13A is formed of a hook member, as the target sheet 12T, it is possible to use one in which many loop threads making engaging projections of the hook member entangled therewith are disposed on a surface of a sheet base material formed of a plastic film or a nonwoven fabric. In a case where the engagement portion 13A is formed of a pressure-sensitive material layer, as the target sheet 12T, it is possible to use one obtained by subjecting a surface of a sheet base material formed of a plastic film having a smooth surface with high pressure-sensitive adhesiveness to a peeling treatment. In addition, in a case where the part to be engaged with the fastening tape 13 in the ventral side portion F is formed of a nonwoven fabric, for example, when the exterior nonwoven fabric 12 in the illustrated example is formed of a nonwoven fabric and the engagement portion 13A of the fastening tape 13 is formed of a hook member, the target sheet 12T can be omitted, and the hook member can be entangled with the nonwoven fabric of the exterior nonwoven fabric 12 to be engaged. In this case, the target sheet 12T may be disposed between the exterior nonwoven fabric 12 and the liquid impervious sheet 11.

(Absorber)

As illustrated in FIGS. 1, 3, 5, 15(a), and 16, the absorber 70 is a portion that absorbs and retains a liquid content of excrement, and includes an upper auxiliary layer 71 disposed at an uppermost portion and a main absorption layer 72 disposed on a back surface side of the upper auxiliary layer 71. FIG. 16 illustrates a layered structure of the absorber 70 in FIG. 15(a) separately for easy understanding. The absorber 70 can be bonded to a member on at least one side of front and back surfaces thereof via an adhesive 50h such as a hot melt adhesive.

(Upper Auxiliary Layer)

The upper auxiliary layer 71 includes a super absorbent nonwoven fabric 42 having a surface exposed on an uppermost surface of the absorber 70 and having a Klemm water absorptiveness of 100 mm or more. The super absorbent nonwoven fabric 42 can quickly absorb and diffuse even a viscous liquid. Therefore, absorbability of the viscous liquid by the absorber 70 can be remarkably improved. The super absorbent nonwoven fabric 42 particularly preferably has a Klemm water absorptiveness of 130 mm or more. In addition, an upper limit of the Klemm water absorptiveness of the super absorbent nonwoven fabric 42 is not particularly limited, but is preferably about 180 mm, and particularly preferably 160 mm.

The water retention amount under a load of the super absorbent nonwoven fabric 42 of the upper auxiliary layer 71 is preferably more than 0 g and 0.15 g or less, and particularly preferably more than 0 g and 0.12 g or less. The water retention amount under no load of the super absorbent nonwoven fabric 42 of the upper auxiliary layer 71 is preferably more than 0 g and 0.7 g or less, and particularly preferably more than 0 g and 0.3 g or less.

The super absorbent nonwoven fabric 42 is not limited by a material and a manufacturing method, but is preferably a wetlaid nonwoven fabric containing 50% or more of pulp fibers or rayon fibers and having a basis weight of 25 to 50 g/m$^2$. As a fiber other than the pulp fiber or the rayon fiber, a synthetic fiber such as a polyolefin-based fiber including polyethylene and polypropylene, a polyester-based fiber, or a polyamide-based fiber (including a composite fiber such as core-sheath in addition to a single component fiber) can be used. Use of such a wetlaid nonwoven fabric is preferable because a viscous liquid can be quickly absorbed and diffused by a capillary phenomenon due to minute fiber gaps. In particular, such a wetlaid nonwoven fabric not only has a high Klemm water absorptiveness but also is very thin and flexible, and therefore can suppress a decrease in flexibility and an increase in thickness as the entire absorber 70. The thickness of the super absorbent nonwoven fabric 42 is not limited, but is preferably about 0.13 to 0.48 mm in a case of the above basis weight.

In addition, as the super absorbent nonwoven fabric 42, a two-layer (illustrated in FIG. 18), three-layer or more multilayer nonwoven fabric including a support layer 42b containing a long fiber of a synthetic resin and a pulp layer 42a located on an outermost side and containing only a pulp fiber is particularly suitable. Such a super absorbent nonwoven fabric 42 can increase strength by presence of the support layer 42b while increasing the Klemm water absorptiveness by the pulp layer 42a, and therefore excellent durability is achieved when the super absorbent nonwoven fabric 42 is disposed at an uppermost portion of the absorber 70.

When the upper auxiliary layer 71 includes first super absorbent polymer particles 43 adjacent to a back surface of the super absorbent nonwoven fabric 42, as illustrated by an arrow in FIG. 17(a), a viscous liquid N absorbed and diffused by the super absorbent nonwoven fabric 42 can be gradually absorbed and retained by the super absorbent polymer particles adjacent to the back surface side of the super absorbent nonwoven fabric 42. As a result, absorbability of the viscous liquid N can be remarkably improved. In particular, when the super absorbent nonwoven fabric 42 of the upper auxiliary layer 71 is the above-described wetlaid nonwoven fabric, delivery of the viscous liquid N to the first super absorbent polymer particles 43 adjacent to the back surface is smooth, which is preferable.

The size and arrangement of the super absorbent nonwoven fabric 42 of the upper auxiliary layer 71 can be appropriately determined. For example, as in the illustrated example, the super absorbent nonwoven fabric 42 may be disposed so as to cover the entire surface of the main absorption layer 72, or may be disposed so as to cover only a part of the surface of the main absorption layer 72, for example, a front end portion, a back end portion, a central portion, or a plurality of portions among these portions. In addition, the super absorbent nonwoven fabric 42 may have a portion protruding from a peripheral edge of the main absorption layer 72, or a part or the whole of a peripheral edge of the super absorbent nonwoven fabric 42 may be separated more closely to a central side than the peripheral edge of the main absorption layer 72. Usually, it is desirable that the super absorbent nonwoven fabric 42 of the upper auxiliary layer 71 covers 90% or more of the area of the main absorption layer 72.

The size and arrangement of a region having the first super absorbent polymer particles 43 can be appropriately determined. For example, as in the illustrated example, the first super absorbent polymer particles 43 may be disposed in the entire region where the super absorbent nonwoven fabric 42 and the main absorption layer 72 overlap each other, or may be disposed only in a part of the region where the super absorbent nonwoven fabric 42 and the main absorption layer 72 overlap each other, for example, at a front end portion, a back end portion, a central portion, or a plurality of portions among these portions. Usually, it is desirable that the region having the first super absorbent polymer particles 43 occupies 83% or more of the area of the main absorption layer 72.

The first super absorbent polymer particles 43 do not have to be fixed to the super absorbent nonwoven fabric 42, but may be fixed thereto. The first super absorbent polymer particles 43 can be bonded to the super absorbent nonwoven fabric 42 with, for example, an adhesive 42h such as a hot melt adhesive applied to a back surface of the super absorbent nonwoven fabric 42 in an intermittent pattern.

The first super absorbent polymer particles 43 do not have to be fixed only by being in contact with a surface of the main absorption layer 72, but are preferably fixed thereto. For example, an adhesive 43h such as a hot melt adhesive is applied to a surface (an upper surface of an upper sheet 51 described later) of the main absorption layer 72 in an intermittent pattern, then the first super absorbent polymer particles 43 are scattered on the adhesive-applied portion, and the super absorbent nonwoven fabric 42 can be disposed on the first super absorbent polymer particles 43 with or without the adhesive 42h interposed therebetween. However, the absorber 70 becomes hard as an application amount of the adhesive 43h is increased. Not only that, but when the first super absorbent polymer particles 43 absorb the liquid to be expanded, the increased application amount of the adhesive 43h inhibits such expansion of the first super absorbent polymer particles 43 such that the first super absorbent polymer particles 43 may be unlikely to attain the original absorption performance. Further, when a non-viscous liquid such as urine is absorbed, it is likely to be difficult for the non-viscous liquid to be supplied from the upper auxiliary layer 71 to the main absorption layer 72, because the adhesive 43h inhibits the permeation of the non-viscous liquid. Therefore, the adhesive 43h is preferably applied to the surface (the upper surface of the upper sheet 51 described later) of the main absorption layer 72 in the intermittent pattern. Further, if the adhesive 43h is applied at an application rate of 4 to 10 g/m$^2$, the permeation of the non-viscous liquid to the main absorption layer 72 may be unlikely to be inhibited, which is preferable.

The basis weight of the first super absorbent polymer particles 43 can be appropriately determined, but is preferably 50 to 150 g/m$^2$ and particularly preferably 40 to 100 g/m$^2$ when a viscous liquid having a small absorption amount required at a time, such as a liquid content in muddy feces, watery feces, or loose feces, is assumed. When the basis weight of the first super absorbent polymer particles 43 is less than 50 g/m$^2$, it may be difficult to sufficiently absorb even a small amount of viscous liquid. In addition, in a case where the basis weight of the first super absorbent polymer particles 43 is more than 150 g/m², when absorbing a large amount of non-viscous liquid such as urine, the first super absorbent polymer particles 43 sufficiently absorb the non-viscous liquid to be expanded, then gel blocking occurs, and there is a high possibility that supply of the non-viscous liquid to the main absorption layer 72 may be inhibited. On the other hand, when the basis weight of the first super absorbent polymer particles 43 is within the above range, even after the first super absorbent polymer particles 43 sufficiently absorb the non-viscous liquid to be expanded, a portion where gel blocking does not occur remains, and supply of the non-viscous liquid to the main absorption layer 72 is secured, which is preferable.

(Main Absorption Layer)

Generally, as the main absorption layer 72, an absorber is used which is obtained by mixing second super absorbent polymer particles 53 (SAP) with hydrophilic short fibers such as fluff pulp and accumulating the mixture in a cotton shape. However, a cell absorbing sheet 50 used in the illustrated example includes a large number of cells 55 (small chambers) which are surrounded by bonded portions 54 of a liquid pervious upper sheet 51 and a lower sheet 52 and in which the upper sheet 51 and the lower sheet 52 are not bonded to each other, and a particulate material which contains the second super absorbent polymer particles 53 and which is contained in the cells 55. Since the absorption performance of the cell absorbing sheet 50 depends on the second super absorbent polymer particles 53, the cell absorbing sheet 50 inevitably has a low absorption speed and low absorbability of the viscous liquid N. Therefore, the above-described upper auxiliary layer 71 particularly has significance when such a cell absorbing sheet 50 is used as the main absorption layer 72.

The cell absorbing sheet 50 will be described in more detail. As illustrated in an enlarged manner in FIGS. 7 and 15(a), the cell absorbing sheet 50 includes the upper sheet 51, the lower sheet 52 disposed on a back surface side of the upper sheet 51, the cells (small chambers) 55 which are surrounded by the bonded portions 54 of the upper sheet 51 and the lower sheet 52 and in which the upper sheet 51 and the lower sheet 52 are not bonded to each other, and the second super absorbent polymer particles 53 contained in the cells 55. The large number of cells 55 are arranged at intervals corresponding to the bonded portions 54. As described above, the large number of cells 55 the entire periphery of which is surrounded by the bonded portions 54 distribute and retain the second super absorbent polymer particles 53. As a result, uneven distribution of the second super absorbent polymer particles 53 in the cell absorbing sheet 50 can be prevented.

In order to facilitate arrangement of the second super absorbent polymer particles 53 at the time of manufacture and to secure a volume of each cell after the second super absorbent polymer particles are expanded by absorption of a liquid, at least one of the upper sheet 51 and the lower sheet 52 in the cell 55 is preferably a concave 50c that is recessed to the outside of the cell 55 in a spread state. However, the second super absorbent polymer particles 53 may be simply sandwiched between the upper sheet 51 and the lower sheet 52 without the concave 50c. The concave 50c is preferably formed in a portion constituting each cell 55 in the upper sheet 51, but may be formed in a portion constituting each cell 55 in the lower sheet 52 as in the example illustrated in FIG. 13(c) and the example illustrated in FIG. 14(c) together with or instead of being formed in a portion constituting each cell 55 in the upper sheet 51. A depth 50d of the concave 50c is not particularly limited, but is preferably about 1.0 to 7.0 mm, and particularly preferably about 1.0 to 5.0 mm.

The concave 50c can be formed by embossing an object sheet. In addition, by this embossing, a convex 50p bulging outward is formed in a portion located at each cell 55 in the object sheet. That is, when the concave 50c is formed in the upper sheet 51 by embossing, the convex 50p bulging upward is formed in a portion located at each cell 55 in the upper sheet 51.

Here, in a case of absorbing the non-viscous liquid U such as urine, when the first super absorbent polymer particles 43 of the upper auxiliary layer 71 are uniformly disposed, the first super absorbent polymer particles 43 preferentially absorb the non-viscous liquid to be expanded, and gel blocking easily occurs in which the expanded first super absorbent polymer particles 43 adhere each other to form a hardly liquid pervious layer. As a result, the non-viscous liquid U may be unlikely to be supplied to the main absorption layer 72. That is, the upper auxiliary layer 71 may inhibit absorption into the main absorption layer 72. On the other hand, as illustrated in FIG. 15(a), when the adhesion amount of the first super absorbent polymer particles 43 on an upper surface of the upper sheet 51 increases from the top of a convex 50p toward the bottom of a valley located between a convex 50p and a convex 50p adjacent to each other, as illustrated in FIG. 17(a), although the first super absorbent polymer particles 43 fixed to the upper surface of the upper sheet 51 can be effectively used for absorbing the viscous liquid N, as illustrated in FIG. 17(b), even after the first super absorbent polymer particles 43 sufficiently absorb the non-viscous liquid U to be expanded, gel blocking is less likely to occur in a portion where the adhesion amount of the first super absorbent polymer particles 43 is smaller, and supply of the non-viscous liquid U to the main absorption layer 72 is therefore less likely to be inhibited, when compared to the same total amount of the used first super absorbent polymer particles uniformly disposed. In addition, by using the convex 50p of the upper sheet 51, it is easy to regularly change the adhesion amount of the first super absorbent polymer particles 43 on the upper surface of the upper sheet 51 (to alternately dispose a portion with a large adhesion amount and a portion with a small adhesion amount). That is, as described above, when a hot melt adhesive is applied to a surface of the main absorption layer 72 in an intermittent pattern and then the first super absorbent polymer particles 43 are scattered on the adhesive-applied portion, the first super absorbent polymer particles 43 easily fall down toward the bottom of the valley due to gravity even if the first super absorbent polymer particles 43 are scattered uniformly. Therefore, the adhesion amount of the first super absorbent polymer particles 43 naturally increases from the top of a convex 50p toward the bottom of a valley located between a convex 50p and a convex 50p adjacent to each other. Therefore, such a non-uniform adhesion structure of the first super absorbent polymer particles 43 is relatively easily manufactured although the structure is complicated at a glance. Note that even in this case, it goes without saying that the basis weight of the first super absorbent polymer particles 43 is preferably within the above-described range.

In this case, as long as the adhesion amount of the first super absorbent polymer particles 43 on the upper surface of the upper sheet 51 increases from the top of a convex 50p toward the bottom of a valley located between a convex 50p and a convex 50p adjacent to each other, the first super absorbent polymer particles 43 do not have to adhere to a part including the top of a convex 50p, and the first super absorbent polymer particles 43 may adhere only to other portions. Alternatively, as in the illustrated example, the first super absorbent polymer particles 43 may adhere to almost an entire portion including the top of a convex 50p and other portions, and the adhesion amount may continuously (or stepwise) increase toward the bottom of a valley.

The size of the convex 50p can be appropriately determined. However, from such a viewpoint, a size 55L of the convex 50p of the upper sheet 51 in the front-back direction LD is preferably 6 to 30 mm, a size 55W of the convex 50p of the upper sheet 51 in the width direction WD is preferably 7 to 50 mm, a width W of the bonded portion 54 is preferably 1.0 to 1.8 mm, and the depth 50d (the height of the convex 50p) of the valley of the upper sheet 51 is preferably 1.0 to 7.0 mm.

On the other hand, as illustrated in FIGS. 7(b), 13(a), and the like, a middle sheet 80 made of a nonwoven fabric is preferably interposed between the upper sheet 51 and the lower sheet 52, but the middle sheet 80 does not have to be disposed as illustrated in FIG. 14(b). When the middle sheet 80 is disposed, three layers of the upper sheet 51, the middle sheet 80, and the lower sheet 52 are bonded to each other at the bonded portion 54. In addition, preferably, the middle sheet 80 is compressed in a thickness direction at a portion located at the bonded portion 54 and bulges up to the inside of the concave 50c at a portion located in the cell 55 (in other words, a fiber density decreases as it goes away from the bonded portion 54). As a result, the concave 50c (and thus the convex) is unlikely to be crushed by a pressure applied in a packaging state of a product or a pressure applied at the time of wearing, and even if the concave 50c is crushed, shape restoration is promoted to at least a portion where the middle sheet 80 has entered or a volume close thereto by elasticity of the middle sheet 80. In addition, at the time of absorbing an excretion liquid, the super absorbent polymer can widen fiber gaps of the middle sheet 80 and can be expanded while entering the fiber gaps, or while easily compressing the middle sheet 80, or while entering the fiber gaps and easily compressing the middle sheet 80. Therefore, presence of the middle sheet 80 is unlikely to inhibit expansion of the second super absorbent polymer particles 53. Furthermore, since the fibers of the middle sheet 80 spreading in the concave 50c secure a liquid passage to each of the second super absorbent polymer particles 53, a decrease in diffusibility is suppressed even after the second super absorbent polymer particles 53 start to be expanded, and gel blocking is unlikely to occur. Therefore, by a synergistic effect thereof, an absorption speed (particularly at an initial stage of absorption) of a disposable diaper including the present cell absorbing sheet 50 is improved.

The upper sheet 51 is not particularly limited as long as the upper sheet 51 is made of a liquid pervious material like the top sheet 30. However, in a case where the first super absorbent polymer particles 43 are fixed with a relatively small amount of a hot melt adhesive 43h applied in an intermittent pattern to the upper surface of the upper sheet 51, the first super absorbent polymer particles 43 easily move, thus when a user touches an external surface of the absorbent article with a hand, gritty and uncomfortable feeling of the first super absorbent polymer particles is likely to be transmitted to the hand. In order to prevent occurrence of such a problem, as illustrated in FIG. 15(b), the upper sheet 51 is preferably formed of a short fiber nonwoven fabric and has a larger amount of fuzz 51f on the upper surface thereof than the lower surface thereof. As a result, the first super absorbent polymer particles 43 are captured among the fuzz 51f (projected fibers) such that the movement of the first super absorbent polymer particles 43 is suppressed, and additionally, the fuzz 51f existing among the first super absorbent polymer particles 43 makes it possible that the absorption of the viscous liquid N and the permeability of the non-viscous liquid U are unlikely to be inhibited. Note that an amount of the fuzz 51f can be measured by a method described in paragraph of the Patent Literature 2.

As the short fiber nonwoven fabric having a larger amount of fuzz 51f on the upper surface thereof than the lower surface thereof, a nonwoven fabric may be used whose fuzz 51f is formed by a raising process. However, this process requires a high cost. Therefore, it is preferable to use, as the upper sheet 51, the air through nonwoven fabric which has the basis weight of 17 to 40 g/m² (particularly, 20 to 30 g/m²) and the thickness of 0.2 to 0.7 mm (particularly, 0.3 to 0.5 mm) and which is configured in such a way that an air-sprayed surface corresponds to the upper surface of the upper sheet 51. As is known in the art, an air through nonwoven fabric is formed by a process in which short fibers are accumulated onto a net to form a web and after that, these short fibers are weld-bonding to each other by heated air (hot air) forced through the web. In the air through nonwoven fabric, the air-sprayed surface (the surface to which heated air is sprayed) is fluffier than a net surface. Therefore, by using the air-sprayed surface of the air-through nonwoven fabric as the upper surface of the upper sheet 51, the movement of the first super absorbent polymer particles 43 can be suppressed by the fuzz 51f provided originally on the upper surface of the upper sheet 51 as illustrated in FIG. 15(b), without the raising process.

The air through nonwoven fabric which is particularly preferable as the upper sheet 51 includes hollow fibers having a fineness of 2.0 to 7.0 dtex in the air-sprayed surface of the air through nonwoven fabric. This is because the air through nonwoven fabric including sufficiently fine hollow fibers in the air-sprayed surface is particularly fluffy on the air-sprayed surface. Eccentric and hollow fibers are preferable because they are much fluffier. Further, the material of the hollow fibers is not particularly limited, but PET is preferable because fuzz made of PET is unlikely to lie down due to the high rigidity thereof. The basis weight of the air through nonwoven fabric used for the upper sheet 51 is not particularly limited, but for example, the basis weight may be 17 to 40 g/m².

The hollow fibers may be included only in a surface layer of the air through nonwoven fabric or may be included in across the entire air through nonwoven fabric in the thickness direction, as long as the hollow fibers are included in the air-sprayed surface of the air through nonwoven fabric. As the former air through nonwoven fabric having the hollow fibers included only in the surface layer, a laminated nonwoven fabric composed of two or more layers including the surface layer in which hollow fibers and non-hollow fibers are mixed can be exemplified. For example, an air through nonwoven fabric including a surface layer in which non-hollow fibers having the fineness of 3.0 to 7.0 dtex and the basis weight of 6 to 17 g/m² and hollow fibers having the fineness of 2.0 to 7.0 dtex and the basis weight of 2 to 9 g/m² are mixed is preferable as the upper sheet 51.

As the lower sheet 52, a material similar to that of the upper sheet 51 can be used, but a liquid impervious material can also be adopted. The liquid impervious material that can be used for the lower sheet 52 can be appropriately selected and used from the materials described in the section of the liquid impervious sheet 11. Although not illustrated, the upper sheet 51 and the lower sheet 52 may be one layer and the other layer in which one material is folded in two.

In a case where the lower sheet 52 is a relatively sparse nonwoven fabric having a fineness of 1.5 to 6.0 dtex, a basis weight of 25 to 50 g/m², and a thickness of 0.1 to 1.0 mm, when the second super absorbent polymer particles 53 in the cell 55 are present on the lower sheet 52 or reach an upper surface of the lower sheet 52, the second super absorbent polymer particles 53 are easily retained between fibers of the lower sheet 52, and are unlikely to move in the cell 55, which is preferable.

The middle sheet 80 is not particularly limited as long as the middle sheet 80 is a nonwoven fabric, but the fineness of fibers constituting the nonwoven fabric is preferably about 1.6 to 7.0 dtex, and more preferably 5.6 to 6.6 dtex. In addition, the porosity of the nonwoven fabric of the middle sheet 80 is preferably 80 to 98%, and more preferably 90 to 95%. When the fineness and the porosity of the middle sheet 80 fall within these ranges, the second super absorbent polymer particles 53 can easily enter the fiber gaps of the middle sheet 80 before absorption of an excretion liquid and during absorption of the excretion liquid while securing elasticity of the middle sheet 80 as much as possible. Therefore, since the fibers of the middle sheet 80 spreading in the concave 50c secure a liquid passage to each of the second super absorbent polymer particles 53 during absorption, a decrease in diffusibility is suppressed even after the second super absorbent polymer particles 53 start to be expanded, and gel blocking is unlikely to occur. The thickness of the middle sheet 80 only needs to be appropriately determined in consideration of the depth 50d of the concave 50c, the degree of enter into the concave 50c, and the like, but is preferably 10% to 90%, and more preferably 70% to 90% of the depth 50d of the concave 50c. The basis weight of the middle sheet 80 only needs to be appropriately determined for the same reason, but is preferably about 25 to 40 g/m² in the thickness range. In order to increase the porosity of the nonwoven fabric of the middle sheet 80 (to widen fiber gaps), the constituent fiber is preferably a crimped fiber. In addition, when the constituent fiber of the nonwoven fabric of the middle sheet 80 is a hydrophilic fiber (including a fiber that has become hydrophilic by a hydrophilizing agent), water retainability is enhanced, and when the constituent fibers are hydrophobic fibers, diffusibility is improved. The fiber bonding method for a nonwoven fabric is not particularly limited, but in order to secure elasticity by sufficiently bonding fibers to each other while increasing the porosity (widening fiber gaps), an air through nonwoven fabric in which fibers are bonded to each other by hot air heating is preferable for the middle sheet 80.

As long as a surface of the middle sheet 80 facing the concave 50c enters the concave 50c, the surface is preferably in contact with an internal surface of the concave 50c as illustrated in FIGS. 13(a) 13(c), 14(a), and 14(c), but the surface may be separated as illustrated in FIG. 13(b). When the surface of the middle sheet 80 facing the concave 50c is separated from the internal surface of the concave 50c, a separation distance 80s thereof can be appropriately determined, but is preferably 30% or less of the depth 50d of the concave 50c. As described above, when a gap is generated in the cell 55, the convex 50p (concave 50c) may be crushed according to the gap in a product state.

As illustrated in FIGS. 13(a) to 13(c) and FIG. 14(a), the middle sheet 80 may be bonded to at least one of the upper sheet 51 and the lower sheet 52 with a hot melt adhesive 80h both in the cell 55 and at the bonded portion 54, or the middle sheet 80 does not have to be bonded to the upper sheet 51 and does not have to be bonded to the lower sheet 52 as illustrated in FIG. 14(c).

Preferably, almost all (for example, 95% or more) of the second super absorbent polymer particles 53 are not fixed to the upper sheet 51, are not fixed to the lower sheet 52, and are not fixed to the middle sheet 80, such that they are freely movable. However, a part or almost all (for example, 95% or more) of the second super absorbent polymer particles 53 can be bonded or can pressure-sensitively adhere to at least one of the upper sheet 51, the lower sheet 52, and the middle sheet 80. FIG. 14(b) illustrates an example in which a part of the second super absorbent polymer particles 53 is bonded to the lower sheet 52 with an adhesive 53h such as a hot melt adhesive. In addition, the second super absorbent polymer particles 53 may be agglomerated to some extent. In particular, in a case where the second super absorbent polymer particles 53 are freely movable in the cell 55, when there is a hollow portion in the cell 55, the second super absorbent polymer particles 53 move in the cell 55 during use, which may cause noise or absorption inhibition due to uneven distribution of the second super absorbent polymer particles 53 in the cell 55. Therefore, in order to solve this, as described above, in one preferable form, the surface of the middle sheet 80 facing the concave 50c is brought into contact with the internal surface of the concave 50c, that is, in other words, substantially the entire cell 55 including the concave 50c is filled with the fibers of the middle sheet 80 having a high porosity. As a result, the second super absorbent polymer particles 53 are captured by the fibers of the middle sheet 80, the second super absorbent polymer particles 53 are pressed against the upper sheet 51 or the lower sheet 52, or the second super absorbent polymer particles 53 are captured by the fibers of the middle sheet 80 and pressed against the upper sheet 51 or the lower sheet 52. Therefore, the second super absorbent polymer particles 53 are unlikely to be freely movable. Therefore, it is possible to prevent noise generation by movement of the second super absorbent polymer particles 53 and absorption inhibition due to uneven distribution of the second super absorbent polymer particles 53 in the cell 55 while preventing expansion inhibition of the second super absorbent polymer particles 53.

As in the examples illustrated in FIGS. 13(a), 13(b), and 14(c), in a case where the second super absorbent polymer particles 53 are most present on an upper surface of the middle sheet 80 and decrease from the upper surface of the middle sheet 80 downward, when a user touches an external surface of the diaper with a hand, a gritty touch (uncomfortable feeling) of the second super absorbent polymer particles 53 is unlikely to be transmitted to the hand due to the interposed middle sheet 80, which is preferable. In particular, when the middle sheet 80 is a bulky nonwoven fabric having a high porosity, the second super absorbent polymer particles 53 can enter fiber gaps of the middle sheet 80 before absorption of an excretion liquid and during absorption of the excretion liquid. Therefore, an absorption speed is further improved. That is, at an initial stage of absorption, absorption proceeds on an upper surface of the middle sheet 80 in which a large number of the second super absorbent polymer particles 53 are distributed, but a speed thereof is limited. Therefore, at the initial stage of absorption, a large amount of an excretion liquid also enters the middle sheet 80 in which a small number of the second super absorbent polymer particles 53 are present, and is absorbed by the second super absorbent polymer particles 53 in the middle sheet 80, temporarily stored until the excretion liquid is absorbed by the second super absorbent polymer particles 53, or diffused into another cell 55 in a periphery. The excretion liquid diffused in the periphery is absorbed by second super absorbent polymer particles 53 present therein in a middle sheet 80, or is sucked up by a large number of second super absorbent polymer particles 53 present above them. Then, in a process in which each of the second super absorbent polymer particles 53 absorbs the excretion liquid, the super absorbent polymer widens fiber gaps, and is expanded while entering the fiber gaps or while compressing the middle sheet 80. By such an absorption mechanism, an excretion liquid is quickly diffused in a wide range of the cell absorbing sheet 50 and is received inside the cell absorbing sheet 50. Therefore, not only the absorption speed is improved, but also a returning prevention property is excellent. In addition, in order to favorably exhibit such an absorption mechanism, the concave 50c is preferably formed at least in a portion constituting each cell 55 in the upper sheet 51.

The degree of distribution of the second super absorbent polymer particles 53 in the cell 55 can be appropriately determined. However, usually, a weight ratio of the second super absorbent polymer particles 53 present on an upper surface of the middle sheet 80 is preferably 50% or more of the total amount, and a weight ratio of the super absorbent polymer retained in the middle sheet 80 (that is, not on the lower sheet 52) is preferably 45% or more of the total amount.

Of course, the distribution of the second super absorbent polymer particles 53 in the cell 55 is not limited thereto. Therefore, as illustrated in FIG. 13(c), the second super absorbent polymer particles 53 can be most present on an upper surface of the lower sheet 52, and can decrease from the upper surface of the lower sheet 52 upward. In addition, as illustrated in FIG. 14(a), the amount of the second super absorbent polymer particles 53 present on each of an upper surface of the middle sheet 80 and an upper surface of the lower sheet 52 may be larger than the amount of the second super absorbent polymer particles 53 present in a portion therebetween. Furthermore, although not illustrated, the second super absorbent polymer particles 53 can be most present in the middle in a thickness direction of the middle sheet 80 and can decrease from the middle upward and downward. This form can be formed by forming the middle sheet 80 as a two-layer nonwoven fabric and sandwiching the second super absorbent polymer particles 53 between the layers.

The basis weight of the second super absorbent polymer particles 53 can be appropriately determined. In the absorber 70 of the present example, since the first super absorbent polymer particles 43 are contained in the upper auxiliary layer 71, the basis weight of the second super absorbent polymer particles 53 in the main absorption layer 72 can be suppressed at a low level. However, it is not appropriate to absorb a relatively large amount of an excretion liquid such as urine only by the upper auxiliary layer 71. Therefore, although it cannot be said unconditionally, the basis weight of the second super absorbent polymer particles 53 is preferably larger than that of the first super absorbent polymer particles 43, and can be, for example, 150 to 350 g/m$^2$. In general, in a case where the basis weight of the second super absorbent polymer particles 53 is less than 150 g/m$^2$, it is difficult to secure an absorption amount, and in a case where the basis weight is more than 350 g/m$^2$, when a user touches an external surface of the product with a hand, a gritty touch (uncomfortable feeling) of the second super absorbent polymer particles 53 is likely to be transmitted to the hand.

The planar shape of the cell 55 can be appropriately determined, and can be a hexagon, a rhombus, a square, a rectangle, a circle, an ellipse, or the like as illustrated in FIG. 8 and the like. However, it is desirable to form the cell 55 into a polygon in order to achieve a denser arrangement, and it is desirable to arrange the cells 55 without a gap as in the illustrated example. Not only cells 55 having the same shape and the same size are arranged, but also a plurality of kinds of cells 55 having different shapes and/or sizes can be arranged in combination, although not illustrated.

A planar arrangement of the cells 55 (that is, similarly, also an aggregate of the second super absorbent polymer particles 53) can be determined appropriately, but a regularly repeated planar arrangement is preferable. In addition to a regularly repeated planar arrangement such as an oblique lattice shape as illustrated in FIG. 12(a), a hexagonal lattice shape (these are also called a zigzag shape) as illustrated in FIG. 12(b), a square lattice shape as illustrated in FIG. 12(c), a rectangular lattice shape as illustrated in FIG. 12(d), or a parallel lattice (a form in which two groups are disposed such that many groups of parallel diagonal rows intersect each other as illustrated in the drawing) shape as illustrated in FIG. 12(e) (including a form in which these are inclined at an angle of less than 90 degrees with respect to a stretchable direction), a form in which a group of the cells 55 (group units may be arranged regularly or irregularly, and may have a pattern shape or a letter shape) is regularly repeated may be adopted.

The size of each cell 55 can be appropriately determined, and for example, the size 55L in the front-back direction LD (equal to the size of the convex 50p in the front-back direction) can be about 6 to 30 mm, and the size 55W in the width direction WD (equal to the size of the convex 50p in the width direction) can be about 7 to 50 mm. The area of each cell 55 can be about 31 to 1650 mm$^2$.

It is desirable that the bonded portion 54 that bonds the upper sheet 51 and the lower sheet 52 to each other is preferably bonded by welding the upper sheet 51 and the lower sheet 52 like ultrasonic welding or heat sealing, but the bonded portion 54 may be bonded via a hot melt adhesive.

The bonded portions 54 of the upper sheet 51 and the lower sheet 52 are disposed so as to surround each cell 55, and can be formed in a dotted line shape (intermittently in a direction surrounding each cell 55) as in the illustrated example or can be formed in a continuous line shape as long as the bonded portion 54 is a boundary between adjacent cells. When the bonded portions 54 are intermittently formed, preferably, the second super absorbent polymer particles 53 are not present or are present in a smaller amount than that in the cell 55 between the bonded portions 54 in a direction surrounding the cell 55. In particular, when the bonded portions are disposed in a dotted line shape (intermittently), the fiber group of the middle sheet passes between adjacent bonded portions and extends between a large number of cells. Therefore, since a liquid diffusion passage is formed between adjacent bonded portions, an absorption speed is improved by improvement of liquid diffusibility between the cells.

As also illustrated in FIG. 10, the bonded portion 54 may be a weak bonded portion 54b that can be peeled off by an expansion force of the second super absorbent polymer particles 53 in the adjacent cell 55, or may be a strong bonded portion 54a that is basically not peeled off by the expansion force of the second super absorbent polymer particles 53 in the adjacent cell 55. In order to cope also with expansion of the second super absorbent polymer particles 53 having a volume equal to or larger than the volume of each cell 55, a part or all of the bonded portions 54 are preferably the weak bonded portions 54*b*. By presence of the weak bonded portion 54*b*, the cells 55 adjacent to each other with the weak bonded portion 54*b* interposed therebetween can be peeled off and coalesced by an absorption expansion pressure of the second super absorbent polymer particles 53 in the cells 55 to form one large cell 55.

Meanwhile, since the strong bonded portion 54*a* is a portion that is basically not peeled off even when the cells 55 on both sides thereof absorb a liquid to be expanded, the strong bonded portion 54*a* has effects of improving diffusibility, preventing flow of a gelled product of the second super absorbent polymer particles 53, reducing a contact area on a surface side, and the like by continuation of the strong bonded portion 54*a* in a specific direction. Therefore, by combining the strong bonded portion 54*a* with the weak bonded portion, the cell absorbing sheet 50 having various characteristics can be constructed as described later. Note that when the bonded portion 54 located on an outermost side in the width direction WD is peeled off, the second super absorbent polymer particles 53 or a gelled product thereof may leak to a side of the cell absorbing sheet 50. Therefore, it is desirable that the bonded portion 54 located on an outermost side in the width direction WD is the strong bonded portion 54*a*. From a similar viewpoint, preferably, the upper sheet 51 and the lower sheet 52 are extended to the outside of a cell 55 forming region in the width direction WD to some extent, and an edge bonded portion 54*c* is formed in the extending portion for reinforcement.

A difference in bonding strength is preferably generated by changing the area of the bonded portion 54 because it is easy, but a method for generating the difference is not limited thereto. For example, when the bonded portion 54 is formed with a hot melt adhesive, it is also possible to adopt a method for making the kind of hot melt adhesive different depending on a site. In particular, when the bonded portion 54 is formed by welding the upper sheet 51 and the lower sheet 52, the weak bonded portion 54*b* can be formed only by forming the bonded portion 54 in a dotted line shape and widening a point interval 54D. However, since the bonded portion 54 is a portion serving as a boundary between the adjacent cells 55, when the point interval 54D is too wide, large gaps are formed at the boundary between the adjacent cells 55, and the second super absorbent polymer particles 53 easily move. Therefore, when the weak bonded portion 54*b* having a dotted line shape is formed by combining the wide or narrow width 54W of the bonded portion 54 and the wide or narrow dot interval 54D, the weak bonded portion 54*b* is easily peeled off although there are small gaps.

The size of the bonded portion 54 that bonds the upper sheet 51 and the lower sheet 52 to each other can be appropriately determined, and for example, the width (which is a size in a direction orthogonal to a direction surrounding the cells 55, and is equal to an interval between the cells 55) 54W can be about 1.0 to 1.8 mm. In addition, when the bonded portion 54 is formed in a dotted line shape (intermittently in a direction surrounding the cells 55), the size 54L of the bonded portion 54 in the direction surrounding the cells 55 is preferably about 0.6 to 1.5 mm, and the point interval 54D is preferably about 0.8 to 3.0 mm. In particular, in a case of the strong bonded portion 54*a*, the width 54W is preferably about 1.3 to 1.8 mm, the size 54L of the bonded portion 54 is preferably about 1.0 to 1.5 mm, and the point interval 54D is preferably about 0.8 to 2.0 mm. In addition, in a case of the weak bonded portion 54*b*, the width 54W is preferably about 1.0 to 1.3 mm, the size 54L of the bonded portion 54 is preferably about 0.6 to 1.0 mm, and the point interval 54D is preferably about 1.5 to 3.0 mm.

In order to make the weak bonded portion 54*b* peelable, the kind and amount of the second super absorbent polymer particles 53 disposed in each cell 55 can be determined such that the volume of the second super absorbent polymer particles 53 in a cell 55 adjacent to the weak bonded portion 54*b* at the time of saturated absorption is sufficiently larger than the volume of the cell 55. In addition, in order to basically make the strong bonded portion 54*a* unpeelable, the kind and amount of the second super absorbent polymer particles 53 disposed in each cell 55 can be determined such that the volume of the second super absorbent polymer particles 53 contained in cells 55 that can be coalesced by peeling of the weak bonded portion 54*b* at the time of saturated absorption is smaller than the volume of the cells 55 after coalescence.

The width of the bonded portion 54 in a case where the bonded portions 54 are formed in a continuous line shape and the width 54W in a case where the bonded portions 54 are formed in a dotted line shape can be constant in a direction surrounding the cells 55 or can be changed. In addition, the shape of each bonded portion 54 in a case where the bonded portions 54 are formed in a dotted line shape can be appropriately determined, and all the bonded portions 54 may have the same shape, or may have different shapes depending on a site. In particular, in a case where the shape of each cell 55 is a polygon, the bonded portion 54 is preferably formed at an intermediate position of each side and/or each vertex position. In addition, it is preferable to form the strong bonded portion 54*a* also at each vertex position. However, in order to proceed coalescence of the cells 55 smoothly, it is preferable to prevent the weak bonded portion 54*b* from being disposed at each vertex position because this would make the weak bonded portion 54*b* be peeled off more easily.

As illustrated in FIGS. 8 and 11, in a region in the middle of the cell absorbing sheet 50 in the width direction WD, a diffusibility improving portion 57 including a longitudinal strong bond line 58 along which the strong bonded portions 54*a* continue in the front-back direction LD and low expansion cells 55*s* adjacent to both sides of the longitudinal strong bond line 58 is preferably disposed. The amount of the second super absorbent polymer particles 53 contained in the low expansion cell 55*s* of the diffusibility improving portion 57 per unit area is smaller than that in each of the cells 55 adjacent to both sides of the diffusibility improving portion 57, and the bonded portion 54 between the low expansion cell 55*s* and each of the cells 55 adjacent to both sides of the diffusibility improving portion 57 is the weak bonded portion 54*b*. In this case, as illustrated in FIG. 10, at the beginning of absorption of an excretion liquid, due to a difference in the expansion amount between the diffusibility improving portion 57 and a periphery portion thereof, a wide groove having the diffusibility improving portion 57 as a bottom portion is formed, and liquid diffusion is promoted by the groove. This state continues until the weak bonded portion 54*b* between the low expansion cell 55*s* of the diffusibility improving portion 57 and each of the cells 55 on both sides thereof is detached due to an expansion force of the second super absorbent polymer particles 53 in the cell 55 around the diffusibility improving portion 57, and the strong bonded portion 54*a* is not detached even after the weak bonded portion 54*b* is detached. Therefore, although the width of the groove is narrowed, the groove having the strong bonded portion 54a as a bottom portion remains, and diffusibility is maintained. That is, the width of the groove is wide at the initial stage of absorption when diffusion of a large amount of an excretion liquid is important. Thereafter, the low expansion cell 55s of the diffusibility improving portion 57 also coalesces with cells 55 in a periphery so as not to cause a problem such as gel blocking, but the groove remains due to the strong bonded portion 54a, and diffusibility improving action is maintained.

The amount of the second super absorbent polymer particles 53 contained in the low expansion cell 55s is preferably ⅓ or less of that in the adjacent cell 55 in terms of weight ratio, and particularly preferably, the second super absorbent polymer particles 53 are not contained at all in the low expansion cell 55s.

Note that in FIGS. 8 and 11, the strong bonded portion 54a is indicated by a thick dotted line, the other weak bonded portion 54b is indicated by a thin dotted line, and a cell 55 containing the second super absorbent polymer particles 53 (that is, a cell 55 other than the low expansion cell 55s and an empty cell 56 described later) is indicated by a hatch pattern in FIG. 11.

The diffusibility improving portion 57 may be disposed over the maximum length of the cell absorbing sheet 50 as illustrated in FIG. 8, or may be disposed only in an intermediate portion (in particular, a range including a crotch portion and extending over both front and back sides thereof) in the front-back direction LD as illustrated in FIG. 11. In addition, as illustrated in FIGS. 8 and 11, the diffusibility improving portion 57 may disposed at one place at the center in the width direction WD, or may be disposed at a plurality of places at intervals in the width direction WD although not illustrated.

When the cells 55 can coalesce with each other over the entire front-back direction LD of the cell absorbing sheet 50, a gelled product of the second super absorbent polymer particles 53 expanded at the time of absorption can largely move in the front-back direction LD in the cells 55 obtained by the coalescence, and the gelled product may gather at a low place such as a crotch portion to deteriorate wearing feeling. Therefore, as illustrated in FIG. 8, it is a preferable form that a plurality of lateral strong bond lines, which is a portion where the strong bonded portions 54a continue continuously or intermittently in the width direction WD or a diagonal direction, is disposed at intervals in the front-back direction LD. As a result, it is possible to prevent movement of the gelled product of the second super absorbent polymer particles 53 in the front-back direction LD by the strong bonded portion 54a that is basically not peeled off at the time of absorption, and it is possible to prevent collapse of the shape of the cell absorbing sheet 50. Of course, as illustrated in FIG. 11, it is also possible to adopt a form in which such a lateral strong bond line 59 is not included.

In particular, as in the form illustrated in FIG. 8, when the longitudinal strong bond lines 58, along which the strong bonded portions 54a continue in the front-back direction LD over the maximum length of the cell absorbing sheet 50, are disposed on both sides in the width direction WD along side edges of the cells 55 located on both outermost sides in the width direction WD and are also disposed in the middle in the width direction WD, and the lateral strong bond lines 59 are portions continuing in the width direction WD or an oblique direction so as to extend between the longitudinal strong bond lines 58 adjacent to each other in the width direction WD, the cells 55 coalesce to fill and not to exceed a maximum expansion section 55G surrounded by the strong bonded portions 54a. Therefore, a gelled product of the second super absorbent polymer particles 53 expanded at the time of absorption does not move out of the maximum expansion section 55G, and shape collapse of the cell absorbing sheet 50 at the time of absorption can be effectively prevented. In addition, liquid diffusibility in a longitudinal direction is improved by the longitudinal strong bond line 58 which is a portion where the strong bonded portions 54a continue in the front-back direction LD, and liquid diffusibility in a lateral direction is improved by the lateral strong bond line 59 along which the strong bonded portions 54a continue in the width direction WD or an oblique direction. For example, in the form illustrated in FIG. 8, if it is assumed that urine is excreted at the position of a reference character Z, the urine diffuses around the position as illustrated in FIG. 9, and the second super absorbent polymer particles 53 at each position absorb the urine. At this time, as illustrated in FIGS. 9 and 10, in the cell 55 in which an expansion pressure of the second super absorbent polymer particles 53 inside is increased, the weak bonded portion 54b around the cell 55 is peeled off without being able to resist the expansion pressure, and coalesces with the adjacent cell 55. This coalescence continues as long as absorption expansion of the second super absorbent polymer particles 53 can peel off the weak bonded portion 54b, and can proceed to the cell 55 having the strong bonded portion 54a in a periphery thereof.

The size, shape, and arrangement (that is, an arrangement of the strong bonded portions 54a) of the maximum expansion section 55G can be appropriately determined. However, when the maximum expansion section 55G is too small, there is no significance in disposing the strong bonded portions 54a. In addition, even if the number of cells 55 is large, when the cells 55 are formed to be elongated, the shape after coalescence of the cells 55 is unlikely to expand.

In the form illustrated in FIGS. 8 to 10, the longitudinal strong bond lines 58 are disposed at a central portion and both side portions of the cell absorbing sheet 50 in the width direction WD, and the lateral strong bond line 59 has a zigzag shape extending in the front-back direction while repeatedly bending left and right between the longitudinal strong bond line 58 at the center and each of the longitudinal strong bond lines 58 at both side portions. As a result, the substantially triangular maximum expansion section 55G having a vertex at the position of the longitudinal strong bond line 58 at the center and the substantially triangular maximum expansion section 55G having a vertex at the position of each of the longitudinal strong bond lines 58 at both sides are alternately and repeatedly formed in the front-back direction. When the lateral strong bond line 59 is formed in a zigzag shape in this manner, it is possible to efficiently promote liquid diffusion in a lateral direction with a small number of the lateral strong bond lines 59, the maximum expansion section 55G has a substantially triangular shape which is likely to expand, and a cell volume increase amount with respect to the number of coalescence of the cells 55 is also excellent, which is preferable.

Only the longitudinal strong bond line 58 can be disposed without disposing the low expansion cell 55s. In this case, since the strong bonded portion 54a is not detached at the time of absorbing an excretion liquid, diffusibility is improved by leaving a groove having the strong bonded portion 54a as a bottom portion.

On the other hand, as illustrated in FIG. 8 and the like, it is also possible to dispose the empty cell 56 having a smaller amount of the second super absorbent polymer particles 53 contained therein per unit area than another cell. In FIG. 11, the cell 55 containing the second super absorbent polymer particles 53 (that is, the cell 55 other than the low expansion cell 55s and the empty cell 56 described later) is indicated by the hatch pattern. Among regions, since each hatch pattern region in FIG. 8 is assumed to be a scattered region 53A of the second super absorbent polymer particles 53 at the time of manufacture, there is a non-hatch pattern portion in the peripheral cell 55. However, when the second super absorbent polymer particles 53 are movable in the cell 55, the positions of the second super absorbent polymer particles 53 in the cell 55 are not fixed in the product, and the second super absorbent polymer particles 53 can be distributed throughout the cell 55 as in the other drawings. The amount of the second super absorbent polymer particles 53 contained in the empty cell 56 is preferably ½ or less of that in another cell in terms of weight ratio, and particularly preferably, the second super absorbent polymer particles 53 are not contained at all in the empty cell 56. For example, since a front end and a back end of the cell absorbing sheet 50 are formed by cut into cell absorbing sheets 50, respectively at the time of manufacture, if the second super absorbent polymer particles 53 are contained at this position, a life of a blade of a cutting device may be shortened. Therefore, it is desirable that at least the cells 55 at the positions corresponding to the front and back ends of the cell absorbing sheet 50 are the empty cells 56. In addition, when the cells 55 on both side portions in the middle of the cell absorbing sheet 50 in the front-back direction LD are the empty cells 56, the portions have less expansion even after absorption. Therefore, the cell absorbing sheet 50 has a shape fitting a periphery of a leg even after absorption.

In the above example, only the second super absorbent polymer particles 53 are contained in the cell 55, but a particulate material other than super absorbent polymer particles, such as deodorant particles, can be contained in the cell 55 together with the second super absorbent polymer particles 53.

(Super Absorbent Polymer Particles)

As the first super absorbent polymer particles 43 and the second super absorbent polymer particles 53, those used for this type of absorbent article can be used as they are. The particle sizes of the first super absorbent polymer particles 43 and the second super absorbent polymer particles 53 are not particularly limited. However, for example, preferably, the ratio of particles having a particle size of more than 500 μm is 30% by weight or less, the ratio of particles having a particle size of 500 μm or less and more than 180 μm is 60% by weight or more, the ratio of particles having a particle size of more than 106 μm and 180 μm or less is 10% by weight or less, and the ratio of particles having a particle size of 106 μm or less is 10% by weight or less. Note that the particle sizes are measured as follows. That is, standard sieves (JIS Z 8801-1:2006) of 500 μm, 180 μm, and 106 μm, and a receiving pan are arranged in this order from the top, 10 g of a sample of super absorbent polymer particles is put into the sieve of 500 μm at the uppermost stage, sieving (shaking for five minutes) is performed, and then the weight of particles remaining on each sieve is measured. As a result of this sieving, the weight ratios of the sample remaining on the sieves of 500 μm, 180 μm, and 106 μm, and the sample remaining on the receiving pan with respect to the input amount are defined as the ratio of particles of more than 500 μm, the ratio of particles of 500 μm or less and more than 180 μm, the ratio of particles of more than 106 μm and 180 μm or less, and the ratio of particles of 106 μm or less, respectively.

As the first super absorbent polymer particles 43 and the second super absorbent polymer particles 53, any material can be used without particular limitation, but those having a water absorption capacity of 40 g/g or more are suitable. Examples of the first super absorbent polymer particles 43 and the second super absorbent polymer particles 53 include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the first super absorbent polymer particles 43 and the second super absorbent polymer particles 53, a usually used particulate material shape is suitable, but other shapes can also be used.

As the first super absorbent polymer particles 43 and the second super absorbent polymer particles 53, those having a water absorption rate of 70 seconds or less, particularly 40 seconds or less are suitably used. When the water absorption rate is too low, so-called returning that a liquid that has been supplied into the absorber 70 returns out of the absorber 70 tends to occur.

In addition, as the first super absorbent polymer particles 43 and the second super absorbent polymer particles 53, those having a gel strength of 1000 Pa or more are suitably used. This makes it possible to effectively suppress a sticky feeling after liquid absorption.

(Wrapping Sheet)

As illustrated in FIGS. 3 and 16(a), the absorber 70 can be wrapped in the wrapping sheet 45. In this case, one wrapping sheet 45 can wrap the absorber 70 in a tubular shape so as to surround front and back surfaces and both side surfaces of the absorber 70, or two wrapping sheets 45 can wrap the absorber 70 so as to sandwich the absorber 70 from both the front and back surface sides of the absorber 70. As the wrapping sheet 45, tissue paper, particularly crepe paper, a nonwoven fabric, a polylaminated nonwoven fabric, a perforated sheet, and the like can be used. However, it is desirable that the wrapping sheet 45 is a sheet from which super absorbent polymer particles do not escape. When a nonwoven fabric is used for the wrapping sheet 45, a hydrophilic SMS nonwoven fabric (SMS, SSMMS, or the like) is particularly suitable, and polypropylene, a polyethylene/polypropylene composite material, or the like can be used as a material thereof. It is desirable that the nonwoven fabric used for the wrapping sheet 45 has a basis weight of 5 to 40 g/m², particularly 10 to 30 g/m².

As illustrated in FIG. 16(b), preferably, the wrapping sheet 45 is wrapped around the absorber 70 from a back surface of the absorber 70 to both side portions of an upper surface of the absorber 70 through both sides of the absorber 70 in the width direction WD, a region 45S not covered with the wrapping sheet 45 is disposed in an intermediate portion of the upper surface of the absorber 70 in the width direction WD, and the upper auxiliary layer 71 is disposed so as to include the entire region 45S. In order to prevent leakage of super absorbent polymer particles at the time of manufacture, before use, or after absorption, the absorber 70 is generally covered with the wrapping sheet 45. However, in the above-described case of the absorber 70 including the upper auxiliary layer 71, it is desirable that the upper auxiliary layer 71 quickly comes into contact with the viscous liquid N. Therefore, as illustrated in FIG. 16(b), it is desirable that a covering range of the wrapping sheet 45 is limited and the upper auxiliary layer 71 is exposed on the upper surface of the absorber 70. Even with such a structure, a portion of the absorber 70 not covered with the wrapping sheet 45 is covered with the super absorbent nonwoven fabric 42 of the upper auxiliary layer 71, and the upper auxiliary layer 71 is based on the super absorbent nonwoven fabric 42 having a high Klemm water absorptiveness (that is, dense). Therefore, an effect of preventing leakage of super absorbent polymer particles is exhibited substantially similar to that of a structure in which the entire absorber 70 is covered with the wrapping sheet 45.

Description of Terms Used in Specification

The following terms used in the specification should be understood to have the meanings defined below unless otherwise specified in the specification.

- "Machine direction: MD" and "cross direction: CD" mean the flow direction (MD) in a manufacturing equipment and the lateral direction (CD) orthogonal to the flow direction, and either one is the front-back direction and the other is the width direction of a product. The MD of a nonwoven fabric is the direction of fiber orientation of the nonwoven fabric. The fiber orientation is a direction along which a fiber of a nonwoven fabric runs and determined by, for example, a measurement method in accordance with the fiber orientation test method based on the zero distance tensile strength of TAPPI standard method T481 or a simple measurement method for determining the fiber orientation direction from the tensile strength ratio of the front-back direction and the width direction.
- "Front-back direction" means a direction (longitudinal direction) indicated by a reference character LD in the drawing, "width direction" means a direction (left-right direction) indicated by a reference character WD in the drawing, and the front-back direction and the width direction are orthogonal to each other.
- "Front surface side" means a side closer to a wearer's skin when an article is worn. "Back surface side" means a side far from a wearer's skin when an article is worn.
- "Front surface" means a surface of a member closer to a wearer's skin when an article is worn. "Back surface" means a surface far from a wearer's skin when an article is worn.
- "Spread state" means a flat spread state without contraction or slackness.
- "Stretch rate" means a value obtained when a natural length is set to 100%. For example, the stretch rate of 200% has the same meaning as the elongation ratio of 2.
- "Artificial urine" is prepared by mixing 2 wt % of urea, 0.8 wt % of sodium chloride, 0.03 wt % of calcium chloride dihydrate, 0.08 wt % of magnesium sulfate heptahydrate, and 97.09 wt % of ion exchanged water, and the mixture is used at a temperature of 37° C. unless otherwise specified.
- "Gel strength" is measured as follows. 1.0 g of super absorbent polymer is added to 49.0 g of artificial urine, and the resulting mixture is agitated with a stirrer. The resulting gel is left in a thermo-hygrostat at 40° C.×60% RH for three hours and then cooled to room temperature. The gel strength of the gel is measured with a curdmeter (Curdmeter-MAX ME-500 manufactured by I. Techno Engineering Co., Ltd.).
- "Basis weight" is measured as follows. After preliminary drying of a sample or a test piece, the sample or the test piece is left in a test room or a test device under normal conditions (an ambient temperature of 23±1° C. and with a relative humidity of 50±2% at the testing site) until the weight of sample or test piece reaches constant mass. Preliminary drying is to achieve the constant mass of the sample or test piece under an environment having a temperature of 100° C. For fibers having a standard moisture regain of 0.0%, preliminary drying may be omitted. The test piece having the constant mass is cut with a cutting template having the size of 100 mm×100 mm into samples having the size of 100 mm×100 mm. The weight of the sample is measured. The measured weight is multiplied by 100 to determine the weight per one square meter, which is defined as the basis weight.
- "Thickness" is automatically measured with an automatic thickness gauge (KES-G5 handy compression tester) under a load of 0.098 N/cm$^2$ and a pressurized area of 2 cm$^2$.
- "Porosity" is measured by the following method. That is, a portion other than a bonded portion in a middle sheet is cut into a rectangle to be used as a sample. The length, width, thickness, and weight of the sample are measured. Using a raw material density of a nonwoven fabric, a virtual weight when the volume is the same as that of the sample and the porosity is 0% is calculated. The sample weight and the virtual weight are put into the following formula to obtain a porosity.

Porosity=[(virtual weight−sample weight)/virtual weight]×100

- "Water absorption capacity" is measured in accordance with JIS K7223-1996 "Testing method for water absorption capacity of super absorbent polymers".
- "Water absorption rate" is defined as "time that elapses before the end point" measured with 2 g of super absorbent polymers and 50 g of normal saline solution in accordance with JIS K7224-1996 "Testing method for water absorption rate of super absorbent polymers".
- "Klemm water absorptiveness" means a Klemm water absorptiveness measured by "Paper and board-Determination of water absorptiveness (capillary rise)-Klemm method" specified in JIS P 8141:2004.
- "Water retention amount" means an amount measured by the following method. A test piece of 10 cm in MD×10 cm in CD (area: 100 cm$^2$) is prepared, and the weight thereof before absorption is measured. Next, the test piece is immersed in artificial urine for five seconds. Thereafter, by picking softly any one of four corners of the test piece with a thumb and an index finger (the test piece is held while the water retained in it is not squeezed out but retained as much as possible), the test piece is lifted downwardly such that the opposing corner is in the lowermost position, and left for 30 seconds until drops of the water are caused to fall. Thereafter, in a case of measuring "water retention amount under a load", this test piece is placed on stacked eight sheets of filter paper (length 150 mm×width 150 mm), and a quadrangular prism-shaped weight (weight 3 kg) having a bottom surface of length 100 mm×width 100 mm is placed on the test piece such that a load is applied to an entire upper surface of the test piece. Then, the weight is removed at the time point when five minutes elapse, and the weight of the test piece after absorption is measured. On the other hand, in a case of measuring "water retention amount under no load", that test piece is placed on stacked eight sheets of filter paper, and nothing is placed thereon. Then, the weight of the test piece after absorption is measured at the time point when five minutes elapse.

Based on these measurement results, a value obtained by converting a difference between the weight after absorption and the weight before absorption into a value per area of 10 cm² is referred to as "water retention amount under a load" or "water retention amount under no load".

The size of each component means a size in a spread state, not a natural length state, unless otherwise specified.

The tests and measurements are carried out in a laboratory or apparatus under normal conditions (a temperature of 23±1° C. and a relative humidity of 50±2% at the testing site), unless the environmental condition for the tests and measurements are otherwise specified.

INDUSTRIAL APPLICABILITY

The present invention is applicable to general absorbent articles such as underpants-type disposable diapers, pad-type disposable diapers, or sanitary napkins, in addition to tape-type disposable diapers as in the above example.

REFERENCE SIGNS LIST

LD Front-back direction
N Viscous liquid
U Non-viscous liquid
WD Width direction
11 Liquid impervious sheet
12 Exterior nonwoven fabric
12T Target sheet
13 Fastening tape
13A Engagement portion
13B Tape main unit portion
13C Tape attachment portion
30 Top sheet
40 Intermediate sheet
42 Super absorbent nonwoven fabric
42a Pulp layer
42b Support layer
43 First super absorbent polymer particles
45 Wrapping sheet
50 Cell absorbing sheet
50c Concave
50d Depth
50p Convex
51 Upper sheet
51f Fuzz
52 Lower sheet
53 Second super absorbent polymer particles
54 Bonded portion
54a Strong bonded portion
54b Weak bonded portion
54c Edge bonded portion
55 Cell
55G Maximum expansion section
55s Low expansion cell
56 Empty cell
57 Diffusibility improving portion
58 Longitudinal strong bond line
59 Lateral strong bond line
60 Rising gather
62 Gather sheet
70 Absorber
71 Upper auxiliary layer
72 Main absorption layer
80 Middle sheet

The invention claimed is:

1. An absorbent article comprising: an absorber; and a liquid pervious top sheet disposed on a front surface side of the absorber, wherein
the absorber includes an upper auxiliary layer disposed at an uppermost portion and a main absorption layer disposed on a back surface side of the upper auxiliary layer,
the upper auxiliary layer includes a super absorbent nonwoven fabric having a surface exposed on an uppermost surface of the absorber and having a Klemm water absorptiveness of 100 mm or more, and first super absorbent polymer particles adjacent to a back surface of the super absorbent nonwoven fabric,
the main absorption layer is a cell absorbing sheet including a liquid pervious upper sheet and a lower sheet, cells which are portions surrounded by bonded portions of the upper sheet and the lower sheet and in which the upper sheet and the lower sheet are not bonded to each other, and a particulate material which contains second super absorbent polymer particles and which is contained in the cells,
the cells are arranged at intervals in the cell absorbing sheet,
the first super absorbent polymer particles are fixed to an upper surface of the upper sheet of the main absorption layer with an adhesive,
the upper sheet is formed of a short fiber nonwoven fabric and has a larger amount of fuzz on the upper surface thereof than a lower surface thereof, and
the adhesive is applied to the upper surface of the upper sheet in an intermittent pattern at an application rate of 4 to 10 g/m².

2. The absorbent article according to claim 1, wherein
in the first super absorbent polymer particles, a ratio of particles having a particle size of more than 500 μm is 30% by weight or less, the ratio of particles having a particle size of 500 μm or less and more than 180 μm is 60% by weight or more, the ratio of particles having a particle size of more than 106 μm and 180 μm or less is 10% by weight or less, and the ratio of particles having a particle size of 106 μm or less is 10% by weight or less, and
a basis weight of the first super absorbent polymer particles on the upper surface of the upper sheet is 40 to 100 g/m².

3. The absorbent article according to claim 2, wherein
a basis weight of the second super absorbent polymer particles in the main absorption layer is 150 to 350 g/m².

4. The absorbent article according to claim 3, wherein
the upper sheet is formed of an air through nonwoven fabric having a basis weight of 17 to 40 g/m² and a thickness of 0.2 to 0.7 mm, and
an air-sprayed surface of the air through nonwoven fabric corresponds to the upper surface of the upper sheet.

5. The absorbent article according to claim 2, wherein
the upper sheet is formed of an air through nonwoven fabric having a basis weight of 17 to 40 g/m² and a thickness of 0.2 to 0.7 mm, and
an air-sprayed surface of the air through nonwoven fabric corresponds to the upper surface of the upper sheet.

6. The absorbent article according to claim 1, wherein
the upper sheet is formed of an air through nonwoven fabric having a basis weight of 17 to 40 g/m² and a thickness of 0.2 to 0.7 mm, and
an air-sprayed surface of the air through nonwoven fabric corresponds to the upper surface of the upper sheet.

7. The absorbent article according to claim 6, wherein the air-sprayed surface of the air through nonwoven fabric includes hollow fibers having a fineness of 2.0 to 7.0 dtex.

\* \* \* \* \*